United States Patent
Muramatsu et al.

(10) Patent No.: US 6,974,685 B2
(45) Date of Patent: *Dec. 13, 2005

(54) HIGH PRODUCTION METHOD OF PRENYL ALCOHOL USING SACCHAROMYCES CELLS

(75) Inventors: Masayoshi Muramatsu, Aichi (JP); Shusei Obata, Aichi (JP); Sakayu Shimizu, Kyoto (JP)

(73) Assignee: Toyota Jidosha Kabushiki Kaisha 1, Toyota (JP)

( * ) Notice: Subject to any disclaimer, the term of this patent is extended or adjusted under 35 U.S.C. 154(b) by 184 days.

This patent is subject to a terminal disclaimer.

(21) Appl. No.: 10/022,434

(22) Filed: Dec. 20, 2001

(65) Prior Publication Data

US 2003/0096385 A1 May 22, 2003

(30) Foreign Application Priority Data

Dec. 28, 2000 (JP) ........................................ 2000-401951
Dec. 10, 2001 (JP) ........................................ 2001-375842

(51) Int. Cl.$^7$ .................................................. C12P 7/02
(52) U.S. Cl. ........................ 435/155; 435/157; 435/171; 435/132
(58) Field of Search ................................ 435/155, 157, 435/171, 132

(56) References Cited

U.S. PATENT DOCUMENTS 6,410,755 B1 * 6/2002 Millis et al. ................. 549/408

FOREIGN PATENT DOCUMENTS

| JP | 2000-69987 | 3/2000 |
| WO | WO 00/01650 | 1/2000 |
| WO | WO 00/01685 | 1/2000 |
| WO | WO 00/01686 | 1/2000 |
| WO | WO 00/016949 | 1/2000 |

OTHER PUBLICATIONS

C. Chambon et al; "Isolation and Properties of Yeast Mutants Affected in Farnesyl Diphosphate Synthetase"; Current Genetics, (1990); pp. 41–46; France.

J. M. Hornby et al; Quorum Sensing in the Dimorphic Fungus Candida albicans is Mediated by Farnesol; Applied; Farnesol from C. Albicans, Applied and Environmental Microbiology; Jul. 2001, p. 2982–2992, vol. 67 No. 7; American Society for Microbiology; USA.

\* cited by examiner

*Primary Examiner*—Irene Marx

(57) ABSTRACT

The present invention provides a high production method of prenyl alcohol, which comprises culturing prenyl alcohol-producing cells in a medium with an increased sugar content in the presence of at least one member selected from the group consisting of a surfactant, a fat or oil, and a terpene to produce and accumulate prenyl alcohol in the cells; allowing the accumulated prenyl alcohol to be secreted from the cells; and then collecting prenyl alcohol. The present invention enables prenyl alcohol to be highly produced in and effectively secreted from prenyl alcohol-producing cells by culturing the cells in a medium with an increased sugar content in the presence of at least one member selected from the group consisting of a surfactant, a fat or oil, and a terpene.

4 Claims, 11 Drawing Sheets

Effects of Tergitol on Geranylgeraniols production

A: culture solution  B: culture solution O.D. 660nm

Control: YM + 20 mg/L ergosterol + 0.05% Tergitol

- ▨ Extracellular FOH
- ☐ Extracellular GGOH
- ■ Intracellular FOH
- ▩ Intracellular GGOH Effects of different surfactants (0.1%) on Geranylgeraniols production A: culture solution    B: culture solution O.D. 660nm Control: YM + 20 mg/L ergosterol + 0.05% Tergitol ▨ Extracellular FOH
■ Intracellular FOH Effects of Adekanol concentrations on Geranylgeraniols production A: culture solution    B: culture solution O.D. 660nm Adekanol is added to YM medium supplemented with 20 mg/L ergosterol and 0.05% Tergitol ▨ Extracellular FOH
■ Intracellular FOH Effects of fats or oils on Geranylgeraniols production A: culture solution    B: culture solution O.D. 660nm None: YM + 20 mg/L ergosterol + 0.05% Tergitol ▨ Extracellular FOH ■ Intracellular FOH Effects of sugars on Geranylgeraniols production A: culture solution    B: culture solution O.D.660nm Extracellular
Intracellular Effects of sugars, fats or oils and surfactants on Geranylgeraniols production

- Extracellular FOH
- Intracellular FOH
- Extracellular GGOH

Effects of soybean oil on farnesol production

A: YM medium supplemented with 5% glucose

B: YM medium supplemented with 5% glucose and 1% soybean oil

ATCC 64031 cells are cultured at a working volume of 5 L

SEQUENCE LISTING

<160> NUMBER OF SEQ ID NOS: 19

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 1
atggaggcca agatagatga gct                                    23

```
<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 2
tcacaattcg gataagtggt cta                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 3
atgccgccgc tattcaaggg act                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 4
ttaggattta atgcaggtga cgg                                              23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 5
atggcttcag aaaagaaat tag                                               23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 6
ctatttgctt ctcttgtaaa ctt                                              23

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 7
tgcatctcga gggccgcatc atgtaattag                                       30

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: PRIMER
```

```
<400> SEQUENCE: 8
cattaggtac cggccgcaaa ttaaagcctt cg                            32

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 9
tgcatctcga gggccgcatc atgtaattag                               30

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: PRIMER

<400> SEQUENCE: 10
cattagggcc cggccgcaaa ttaaagcctt cg                            32

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: PRIMER

<400> SEQUENCE: 11
cacggagctc cagttcgagt ttatcattat caa                           33

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: PRIMER

<400> SEQUENCE: 12
ctctccgcgg tttgtttgtt tatgtgtgtt tattc                         35

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: PRIMER

<400> SEQUENCE: 13
tccccgcgga tggaggccaa gatagat                                  27

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: PRIMER

<400> SEQUENCE: 14
gcagggaccc caattcggat aagtggtc                                 28

<210> SEQ ID NO 15
<211> LENGTH: 29
```

```
-continued

<212> TYPE: DNA
<213> ORGANISM: Artificial Sequence
<220> FEATURE:
<223> OTHER INFORMATION: Description of Artificial Sequence: PRIMER

<400> SEQUENCE: 15
gtagggtcct cagaaaaaga aattaggag                                          29

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: PRIMER

<400> SEQUENCE: 16
tgtaaaacga cggccagt                                                      18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 17
taatacgact cactataggg                                                    20

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: PRIMER

<400> SEQUENCE: 18
agaagatacg gatttctttt ctgcttt                                            27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: PRIMER

<400> SEQUENCE: 19
aactttggtg caaattgggt caatgat                                            27
```

HIGH PRODUCTION METHOD OF PRENYL ALCOHOL USING SACCHAROMYCES CELLS

FIELD OF THE INVENTION

The present invention relates to a high production method of prenyl alcohol using microorganisms.

BACKGROUND OF THE INVENTION

Geranylgeraniol and farnesol, typical members of prenyl alcohol, are believed to be produced in organisms through hydrolysis of geranylgeranyl pyrophosphate and farnesyl pyrophosphate with a phosphatase. Geranylgeranyl pyrophosphate is a pyrophosphate ester of geranylgeraniol, which is yielded by condensation between isopentenyl pyrophosphate and farnesyl pyrophosphate or condensation between three molecules of isopentenyl pyrophosphate and dimethyl aryl pyrophosphate. Geranylgeranyl pyrophosphate is metabolized into a diterpene compound (e.g., gibberellin) by cyclization, into a carotenoid compound via phytoene formed by tail-to-tail condensation, or into polyprenylpyrophosphate by head-to-tail condensation with isopentenyl pyrophosphate. On the other hand, farnesyl pyrophosphate is yielded by condensation between isopentenyl pyrophosphate and geranyl pyrophosphate or condensation between two molecules of isopentenyl pyrophosphate and dimethyl aryl pyrophosphate. Farnesyl pyrophosphate is metabolized into a sesquiterpene compound by cyclization, into steroid and triterpene compounds via squalene formed by tail-to-tail condensation, or into polyprenylpyrophosphate or dolichol by head-to-tail condensation with isopentenyl pyrophosphate. It is also metabolized into a prenylated protein when linked to a cysteine residue of a specific protein such as Ras protein or G protein. Thus, a series of geranylgeraniol derivatives, including geranylgeraniol, geranylgeranyl pyrophosphate and precursors thereof, i.e., farnesyl pyrophosphate, farnesol, geranyl pyrophosphate or geraniol, are dominant compounds as biosynthetic intermediates of terpenes, carotenoids or steroids. In addition, geranylgeraniol and analogous compounds thereof are important for use in the production of perfume, a taxane compound having an anti-tumor activity (Japanese Patent Application No. 8-227481), a hair tonic (Japanese Patent Application No. 8-180449), a therapeutic agent for osteoporosis (Japanese Patent Application No. 9-294089) and the like.

In the production of the geranylgeraniol derivatives stated above, an erg mutant of *Saccharoinyces cerevisiae* is known to produce and secrete farnesol [Curr. Genet., 18, 41–46 (1990)], but this mutant is not practical for use because it provides a low farnesol production (1 mg/L). Also, there has been developed a technique for producing an arachidonate-containing lipid by culturing a mutant derived from a microorganism having the ability to produce an arachidonate-containing lipid in a medium supplemented with a hydrocarbon, a fatty acid, and/or a fat or oil (Japanese Patent Application Laid-Open (kokai) No. 2000-69987). However, the above supplemental ingredients are only used for conversion into arachidonate (i.e., used as precursors for a final product) or consumed as nutrient sources, and therefore have no effect on extracting a substance produced in the mutant cells.

To produce an useful substance, it is often advantageous to use an elevated energy level for synthesis and an increased concentration of sugar as a starting material. However, when an oily substance is to be produced under an increased sugar concentration, since it has poor permeability through a cell membrane, the oily substance accumulates in cells, thereby inducing product inhibition. In such a case, the oily substance is not expected to be produced at a high yield.

SUMMARY OF THE INVENTION

Accordingly, the object of the present invention is to provide a method for effective secretory production of prenyl alcohol using a microorganism capable of producing prenyl alcohol, which involves allowing prenyl alcohol accumulated in the microorganism to be secreted into an extracellular environment.

Our research efforts were directed to achieving the above object, and we have found that when cells capable of producing prenyl alcohol, such as yeast cells (ascomycetes and deuteromycetes), bacterial cells, actinomycete cells and filamentous fungus cells, are cultured in a medium with an increased sugar content in the presence of at least one member selected from the group consisting of a surfactant, a fat or oil, and a terpene, prenyl alcohol accumulated in the cells can be actively secreted into an extracellular environment to reduce intracellular product concentration, thereby effecting an improvement in productivity per se. Surprisingly, we further have found that cells belonging to the above-mentioned microorganisms which do not produce prenyl alcohol under normal culture conditions also enable the production of the compound when cultured under the same conditions as stated above, thereby finally completing the invention.

Namely, the present invention provides a high production method of prenyl alcohol, which comprises culturing prenyl alcohol-producing cells belonging to any one of the following genera:

Saccharomyces,
Saccharomycopsis,
Saccharomycodes,
Schizosaccharomyces,
Wickerhamia,
Debaryomyces,
Hansenula,
Hanseniaspora,
Lypomyces,
Pichia,
Kloeckera,
Candida,
Zygosaccharomyces,
Ogataea,
Kuraishia,
Komagataella,
Yarrowia,
Bacillus,
Staphylococcus,
Pseudomonas,
Williopsis,
Nakazawaea,
Kluyveromyces,
Torulaspora,
Citeromyces,
Waltomyces,
Micrococcus,

*Cryptococcus,*
*Exiguobacterium,*
*Nocardia,*
*Mucor,*
*Ambrosiozyma,*
*Cystofilobasidium,*
*Metschnikowia,*
*Trichosporon,*
*Xanthophyllomyces,*
*Bullera,*
*Fellomyces,*
*Filobasidium,*
*Holtermannia,*
*Phaffia,*
*Rhodotorula,*
*Sporidiobolus,*
*Sporobolomyces,*
*Willopsis,*
*Zygoascus,*
*Haloferax,*
*Brevibacterium,*
*Leucosporidium,*
*Myxozyma,*
*Trichosporiella,* and
*Alcaligenes* in a medium with an increased sugar content in the presence of at least one member selected from the group consisting of a surfactant, a fat or oil, and a terpene to produce and accumulate prenyl alcohol in the cells; allowing prenyl alcohol to be secreted from the cells; and then collecting prenyl alcohol.

This specification includes part or all of the contents as disclosed in the specification and/or drawings of Japanese Patent Application Nos.2000-401951 and No.2001-375842, which are priority documents of the present application.

DETAILED DESCRIPTION OF THE INVENTION

Figure 1:
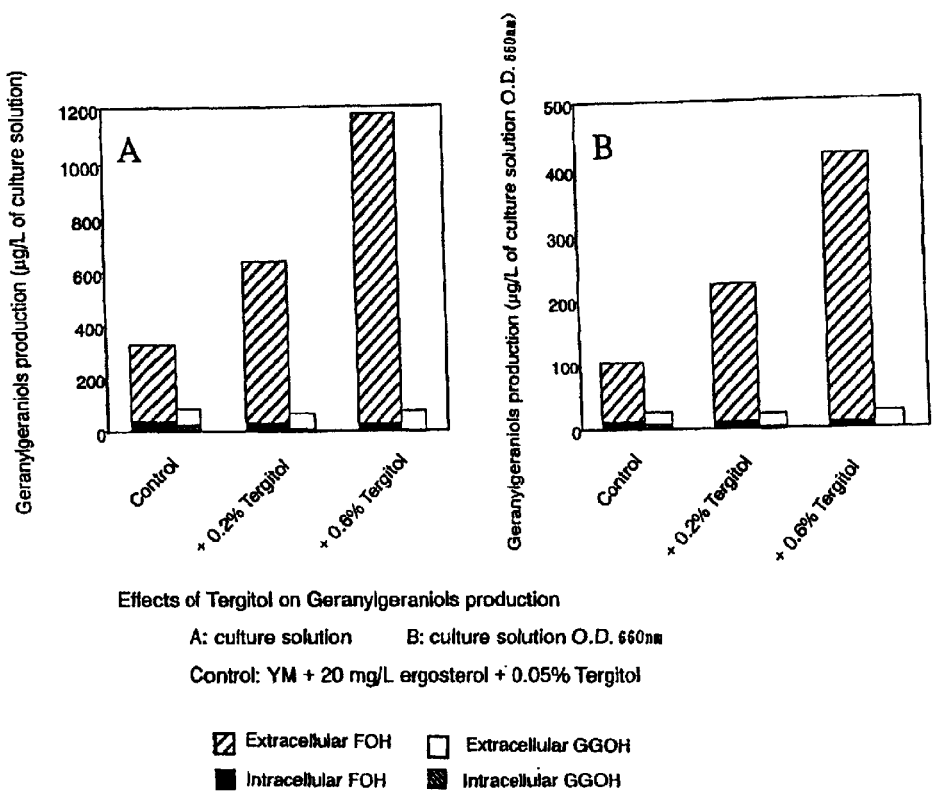
FIG. 1 shows effects of a surfactant on geranylgeraniol and farnesol secretory production (A: culture solution; B: culture solution O.D.).

The present invention will be described below in more detail.

In the present invention, a microorganism fermentation method is used to produce prenyl alcohol, typically geranylgeraniol and analogous compounds thereof. As used herein, an analogous compound of geranylgeraniol refers to geranylgeranyl pyrophosphate and compounds produced in association with the synthesis thereof, i.e., farnesyl pyrophosphate, farnesyl monophosphate, farnesol, geranyl pyrophosphate, geranyl monophosphate, geraniol, nerolidol, geranyllinanol, linalool and the like.

In the present invention, any microorganism may be used for geranylgeraniol production, so long as it has a potential ability to produce geranylgeraniol. Examples include yeast strains belonging to any one of *Saccharomyces, Saccharomycopsis, Saccharomycodes, Schizosaccharomyces, Wickerhamia, Debaryomyces, Hansenula, Hanseniaspora, Pichia, Kloeckera, Candida, Zygosaccharomyces, Ogataea, Kuraishia, Komagataella, Yarrowia, Williopsis, Nakazawaea, Kluyveromyces, Torulaspora, Cryptococcus, Bullera, Rhodotorula, Sporobolomyces, Kloeckera* and *Willopsis*; filamentous fungus strains belonging to *Mucor*; archaebacterial strains belonging to *Haloferax*; or bacterial strains belonging to Alcaligenes.

Specific examples of geranylgeraniol-producing cells will be presented below:

(1) *Saccharomyces:*
   *Saccharomyces cerevisiae* strains ATCC 12341, IFO 0565, IFO 0222, ATCC 64031, ATCC 76625, 4104 (Kyoto Univ.), 4045 (Kyoto Univ.), 4103 (Kyoto Univ.), 4104 (Kyoto Univ.), ATCC 9080, IFO 1346, ATCC 204660, IFO 0538 and IFO 0210, *Saccharomyces ellipsoideus* strain 4102 (Kyoto Univ.), *Saccharomyces sake* strains 4023 (Kyoto Univ.) and Kyokai No. 2, *Saccharomyces rosei* strain IFO 0252, *Saccharomyces peka, Saccharomyces kluyveri* strain IFO 18921, and *Saccharomyces Hafe logos van Laer* strain 3009 (Kyoto Univ.);

(2) *Saccharomycopsis:*
   *Saccharomycopsis fibuligera* strain IFO 0106;

(3) *Saccharomycodes:*
   *Saccharomycodes ludwigii* strain IFO 0339;

(4) *Schizosaccharomyces:*
   *Schizosaccharomyces octosporus* strain IAM 4842, and *Schizosaccharomyces pombe* strains IFO 0346 and IFO 0638;

(5) *Wickerhamia:*
   *Wickerhamia fluorescens* stain IFO 1116;

(6) *Debaryomyces:*
   *Debaryomyces hansenii* var. *fabryi* strain IFO 0794, *Debaryomyces castellii* strain IFO 1359, and *Debaryomyces vanrijiae* var. *vanrijiae* strain JCM 2169;

(7) *Hansenula:*
   *Hansenula valbyensis, Hansenula saturnus, Hansenula beijerinckii, Hansenula matritensis, Hansenula capsulata, Hansenula polynmorpha, Hansenula polymopla;*

(8) *Hanseniaspora*:
　*Hanseniaspora valbyensis* strain IFO 0115;
(9) *Pichia*:
　*Pichia membranaefaciens* strain IFO 0128, *Pichia aganobii, Pichia naganishii* strain IFO 1670, *Pichia silvicola* strain IFO 0807, *Pichia anomala* strains IFO 0118, IFO 0569 and IFO 0707, and *Pichia pastoris* strain ATCC 20864;
(10) *Kloeckera*:
　*Kloeckera japonica* strain IFO 0151;
(11) *Candida*:
　*Candida krusei* strain IFO 0013, *Candida kefyr* strain IFO 0706, *Candida tenuis* strain IFO 0716, *Candida solani* strain IFO 0762, *Candida glabrata* strains IFO 0005 and IFO 0622, *Candida albicans* strain IFO 1060, *Candida zeylanoides* strain IFO 0719, *Candida catenulata* strain IFO 0720, *Candida cariosilignicola* strain IFO 1910, *Candida stellata* strain IFO 0701, and *Candida utilis* strain IFO 0619;
(12) *Zygosaccharomyces*:
　*Zygosaccharomyces rouxii* strains IFO 0487 and IFO 0686, and *Zygosaccharomyces japanicus* strain IFO 0595;
(13) *Ogataea*:
　*Ogataea glucozyma* strain IFO 1472, and *Ogataea polymorpha* strain IFO 1475;
(14) *Kuraishia*:
　*Kuraishia capsulata* strain IFO 0974;
(15) *Komagataella*:
　*Komagataella pastoris* strain IFO 0948;
(16) *Yarrowia*:
　*Yarrowia lopolytica* strain IFO 0717;
(17) *Williopsis*:
　*Williopsis saturnus* var. *saturnus* strains IFO 0125 and IFO 0941, and *Williopsis saturnus* strain IFO 0895;
(18) *Nakazawaea*:
　*Nakazawaea holstii* strain IFO 0980;
(19) *Kluyveromyces*:
　*Kluyveromyces marxianus* strains IFO 0617 and IFO 0288, *Kluyveromyces thermotolerans* strain IFO 0662, and *Kluyveromyces lactis* strain IFO 0648;
(20) *Torulaspora*:
　*Torulaspora delbrueckii* strain IFO 0422;
(21) *Cryptococcus*:
　*Cryptococcus humicolus* strain IFO 1527;
(22) *Mucor*:
　*Mucor javanicus* strain IFO 4570;
(23) *Bullera*:
　*Bullera pseudoalba* strain IFO 10179;
(24) *Rhodotorula*:
　*Rhodotorula minuta* strain IFO 0715, and *Rhodotorula rubra* strain IFO 0870;
(25) *Sporobolomyces*:
　*Sporobolomyces salmonicolor* strain IFO 0374;
(26) *Haloferax*:
　*Haloferax volcanii* strain IFO 14742; and
(27) *Alcaligenes*:
　*Alcaligenes faecalis* strain IFO 13111.

In the present invention, any microorganism may be used for farnesol production, so long as it has a potential ability to produce farnesol. Examples include yeast strains belonging to any one of *Saccharomyces, Saccharomycodes, Schizosaccharomyces, Wickerharnia, Debaryomyces, Hanseniaspora, Lypomyces, Pichia, Candida, Ogataea, Kuraishia, Komagataella, Yarrowia, Kluyveromyces, Torulaspora, Zygosaccharomyces, Williopsis, Citeromyces, Waltomyces* and *Cryptococcus*; bacterial strains belonging to any one of *Bacillus, Staphylococcus, Pseudomonas, Micrococcus* and *Exiguobacterium;* actinomycete strains belonging to *Nocardia;* filamentous fungus strains belonging to *Mucor;* or microbial strains belonging to any one of *Ambrosiozyma, Cystofilobasidium, Metschnikowia, Trichosporon, Xanthophyllomyces, Bullera, Fellomyces, Filobasidium, Holtermannia, Phaffia, Sporidiobolus, Sporobolomyces, Willopsis, Zygoascus, Leucosporidium, Myxozyma, Trichosporiella, Haloferax* and *Brevibacterium*.

Specific examples of farnesol-producing cells will be presented below:
(1) *Saccharomyces*:
　*Saccharomyces cerevisiae* strains IFO 1346, ATCC 204660, IFO 0258, IFO 0565, ATCC 64031, ATCC 76625, IFO 0262, IFO 0538, 4104 (Kyoto Univ.), 4045 (Kyoto Univ.), 4103 (Kyoto Univ.), IFO 0210 and IFO 2347, *Saccharomyces unisporus* strain IFO 0215, *Saccharomyces sake* strain Kyokai No. 2, *Saccharoinyces ellipsoideus* strain 4102 (Kyoto Univ.), *Saccharoinyces rosei* strain IFO 0252, *Saccharomyces logos* strain 4101 (Kyoto Univ.), *Saccharomyces dairensis, Saccharomyces bayanus* strains IFO 0539 and IFO 0613, *Saccharomyces kluyveri* strain IFO 1892, *Saccharomyces paradoxus* strain IFO 0259, and *Saccharomyces Hafe logos van Laer* strain 4003 (Kyoto Univ.);
(2) *Saccharomycodes*:
　*Saccharomycodes ludwigii* strain IFO 0339;
(3) *Schizosaccharomyces*:
　*Schizosaccharomyces pombe* strains IFO 0346, IFO 0638 and IFO 0358, and *Schizosaccharomyces octosporus* strain IAM 4842;
(4) *Hanseniaspora*:
　*Hanseniaspora valbyensis* strain IFO 0115;
(5) *Debaryomyces*:
　*Debaryomyces hansenii* strain IFO 0023, *Debaryomyces hansenii* var. *fabryi* strain IFO 0749, *Debaryomyces castellii* strain IFO 1359, and *Debaryomyces vanrijiae* var. *vanrijiae* strain JCM 2169;
(6) *Lypomyces*:
　*Lypomyces starkeyi* strain IFO 0678;
(7) *Pichia*:
　*Pichia aganobii* strain 4261 (Kyoto Univ.), *Pichia naganishii* strain IFO 1670, *Pichia anomala* strains IFO 0118, IFO 0569, IFO 0963, IFO 707 and IFO 0146, and *Pichia pastoris* strain ATCC 20864;
(8) *Candida*:
　*Candida utilis* strains IFO 0626 and IFO 0619, *Candida albicans* strains IPO 0579 and IFO 1060, *Candida zeylanoides* strain IFO 0719, *Candida glabrata* strains IFO 0005, IFO 0622 and IFO 0741, *Candida cariosilignicola* strain IFO 1910, *Candida stellata* strain IFO 0701, *Candida solani* strain IFO 0762, *Candida intermedia* strain IFO 0761, *Candida krusei* strain IPO 0941 and *Candida tenuis* strain IFO 0716;
(9) *Wickerharnia*:
　*Wickerhamia fluoresces* strain IFO 1116;
(10) *Kuraishia*:
　*Kuraishia capsulata* strain IFO 0974;
(11) *Komagataella*:
　*Komagataella pastoris* strain IFO 0948;

(12) *Ogataea*:
  *Ogataea glucozyma* strain IFO 1472, *Ogataea polymorpha* strain IFO 1475;
(13) *Yarrowia*:
  *Yarrowia lopolytica* strain IFO 0717;
(14) *Kluyveromyces*:
  *Kluyveromyces marxianus* strains IFO 0288 and IFO 0617, *Kluyveromyces thermotolerans* strain IFO 0662, and *Kluyveromyces lactis* strain IFO 0648;
(15) *Torulaspora*:
  *Torulaspora delbrueckii* strain IFO 0422;
(16) *Zygosaccharomyces*:
  *Zygosaccharomyces rouxii* strains IFO 0487 and IFO 0686, *Zygosaccharomyces japanicus* strain IFO 0595, and *Zygosaccharomyces fermentati* strain IFO 0021;
(17) *Williopsis*:
  *Williopsis saturnus* var. *saturnus* strain IFO 0941, *Williopsis californica* strain IFO 0800 and *Willopsis saturnus* strain IFO 0895;
(18) *Citeromyces*:
  *Citeromyces matritensis* strain IFO 0954;
(19) *Waltomyces*:
  *Waltomyces lipoder* strain IFO 0673;
(20) *Cryptococcus*:
  *Cryptococcus humicolus* strain IFO 1527;
(21) *Bacillus*:
  *Bacillus amyloliquefaciens* strain IFO 3022, and *Bacillus pumilus* strain IFO 3030;
(22) *Staphylococcus*:
  *Staphylococcus epidermidis* strain IFO 3762;
(23) *Pseudomonas*:
  *Pseudomonas* sp. strain 876 (Kyoto Univ.);
(24) *Micrococcus*:
  *Micrococcus luteus* strain IFO 3067;
(25) *Exiguobacterium*:
  *Exiguobacterium acetylicum* strain IFO 12146;
(26) *Nocardia*:
  *Nocardia asteroides* strain 2103 (Kyoto Univ.);
(27) *Mucor*:
  *Mucor Javanicus* strain IFO 4570;
(28) *Ambrosiozyma*:
  *Ambrosiozyma platypodis* strain IFO 10752;
(29) *Cystofilobasidium*:
  *Cystofilobasidium infirmominiatum* strain IFO 1057;
(30) *Leucosporidium*:
  *Leucosporidium scottii* strain IFO 1924;
(31) *Metschnikowia*:
  *Metschnikowia lunata* strain IFO 1605;
(32) *Myxozyma*:
  *Myxozyma lipomycoides* strain IFO 10351;
(33) *Trichosporon*:
  *Trichosporon pullulans* strain IFO 1232;
(34) *Xanthophyllomyces*:
  *Xanthophyllomyces dendrorhous* strain IFO 10130;
(35) *Bullera*:
  *Bullera pseudoalba* strain IFO 10179;
(36) *Fellomyces*:
  *Fellomyces penicillatus* strain IFO 10119;
(37) *Filobasidium*:
  *Filobasidium capsuligenum* strain IFO 1185, and *Filobasidium uniguttulatum* strain IFO 0699;
(38) *Kloeckera*:
  *Kloeckera corticis* strain IFO 0633;
(39) *Holtermannia*:
  *Holtermannia corniformis* strain IFO 10742;
(40) *Phaffia*:
  *Phaffia rhodozyma* strain ATCC 66270;
(41) *Saccharomycopsis*:
  *Saccharomycopsis ferinentans* strain IFO 10772;
(42) *Sporidiobolus*:
  *Sporidiobolus samonicolar* strain IFO 1035;
(43) *Sporobolomyces*:
  *Sporobolomyces salmonicolor* strain IFO 0374;
(44) *Trichosporiella*:
  *Trichosporiella flavificans* strain IFO 1573;
(45) *Zygoascus*:
  *Zygoascus hellenicus* strain IFO 10184;
(46) *Haloferax*:
  *Haloferax volcanii* strain IFO 14742; and
(47) *Brevibacterium*:
  *Brevibacterium linens* strain IFO 12171.

In the present invention, any microorganism may be used for nerolidol production, so long as it has a potential ability to produce nerolidol. Examples include yeast strains belonging to *Saccharomyces* or *Candida*; filamentous fungus strains belonging to *Mucor*; or microbial strains belonging to any one of *Cystofilobasidium*, *Rhodotorula*, *Willopsis*, *Zygoascus* and *Haloferax*.

Specific examples of nerolidol-producing cells will be presented below:
(1) *Saccharomyces*:
  *Saccharomyces unisporus* strain IFO 0215, *Saccharomyces cerevisiae* strains 4045 (Kyoto Univ.), 4103 (Kyoto Univ.), 4104 (Kyoto Univ.), IFO 0210 and ATCC 64031, *Saccharomyces Hafe logos van Laer* strain 4003 (Kyoto Univ.), and *Saccharomyces elliposoideus* strain 4102 (Kyoto Univ.);
(2) *Candida*:
  *Candida grabrata* strains IFO 0622, IFO 0005 and IFO 0741, *Candida solani* strain IFO 0762, *Candida cariosilignicola* strain IFO 1910, and *Candida krusei* strain IFO 0941;
(3) *Mucor*:
  *Mucor Javanicus* strain IFO 4570;
(4) *Cystofilobasidium*:
  *Cystofilobasidium infirmominiatum* strain IFO 1057;
(5) *Rhodotorula*:
  *Rhodotorula minuta* strain IFO 0715, and *Rhodotorula rubra* strain IFO 0870;
(6) *Willopsis*:
  *Williopsis californica* strain IFO 0800; and
(7) *Haloferax*:
  *Haloferax volcanii* strain IFO 14742.

In addition to the above-listed microorganisms, further examples of microorganisms capable of producing prenyl alcohol such as geranylgeraniol, farnesol and/or nerolidol, which can be used in the present invention, include microbial strains belonging to any one of *Dipodascus, Issatchenkia, Mortierella, Rhodosporidium, Tsukamurella, Yamadazyma, Bensingtonia, Botryozyma, Brettanomyces, Clavispora, Dekkera, Eremascus, Eremothecium, Erythrobasidium, Kloeckeraspora, Kockovaella, Kodamaea, Kurtzmanomyces, Lodderomyces, Malassezia, Mrakia, Nadsonia, Pachysolen, Saturnispora, Schizoblastosporion, Sporopachydermia, Stephanoascus,*

*Sterigmatomyces, Sterigmatosporidium, Sympodiomyces, Sympodiomycopsis, Trigonopsis, Tsuchiyaea, Zygozyma* and *Aciculoconidium*.

The microorganisms used in the present invention also encompass recombinant microorganisms modified by gene transfer into the naturally occurring microorganisms listed above.

Culture of the microorganisms used in the present invention will be described in turn. In general, any medium may be used to culture the microorganisms, so long as it allows the growth of these microorganisms. Specific examples include YM medium, KY medium and F101 medium for culture of yeast cells (ascomycetes and deuteromycetes); and KB medium for culture of bacterial cells, actinomycete cells and filamentous fungus cells.

Any carbon compound may be used as a carbon source, so long as the microorganisms can assimilate it for growth.

As a nitrogen source, for example, an inorganic nitrogen source including ammonium sulfate, ammonium chloride or ammonium nitrate, or an organic nitrogen source including yeast extract, peptone or meat extract may be used. In addition to these, a medium may further contain minerals, metal salts, and/or vitamins, if necessary.

Culture conditions will vary depending on the types of microorganisms. In general, the culture may preferably be performed at a temperature of 20° C. to 40° C., more preferably 25° C. to 35° C., and at a pH of 5 to 9. The culture may also be performed under anaerobic or aerobic conditions according to the types of microorganisms, preferably performed under aerobic conditions with shaking or rotating because aerobic conditions permit a higher growth speed than anaerobic conditions.

However, it is naturally important to select culture conditions for maximum production of prenyl alcohol, according to the type of microorganism to be used and the composition of the medium.

In the present invention, the prenyl alcohol-producing cells are cultured in a medium with an increased sugar content in the presence of at least one member selected from the group consisting of a surfactant, a fat or oil, and a terpene in order to improve prenyl alcohol production and stimulate product secretion from the cells.

As used herein, a "medium with an increased sugar content" means a medium having a sugar content of 2% to 7%. Examples of sugars include glucose, sucrose and the like. As used herein, the percentage (%) used to express a sugar content etc. is based on w/v (%).

Examples of a fat or oil used in the present invention include soybean oil, fish oil, almond oil, olive oil and the like. For example, it may be added to a medium at a concentration of 0.01% or more, preferably 1% or more. Since a concentration exceeding 3% gives no further effect, it is desirable to add a fat or oil at a concentration of 0.01% to 3% in view of cost.

In the present invention, a preferred surfactant is a non-ionic surfactant including polyethylene glycol-type surfactants (e.g., an ethylene oxide adduct of a higher alcohol, an ethylene oxide adduct of an alkylphenol, an ethylene oxide adduct of a fatty acid, an ethylene oxide adduct of a polyhydric alcohol fatty acid ester, an ethylene oxide adduct of a higher alkylamine, an ethylene oxide adduct of a fatty amide, an ethylene oxide adduct of polypropylene ethylene glycol), polyhydric alcohol-type surfactants (e.g., a fatty acid ester of sucrose, an alkylether of a polyhydric alcohol), or a silicone oil (e.g., dimethyl silicone, a polyether-modified silicone oil).

More specifically, the following commercially available surfactants can be used in the present invention: Tergitol NP-40 (Nacalai), cholic acid (Nacalai), deoxycholic acid (Nacalai), N-lauryl sarcosine (Nacalai), sucrose monolaurate (Nacalai), Triton X-100 (Nacalai), Triton X-305 (Nacalai), Nonidet P-40 (Iwai Chemicals Company), Tween 20 (Nacalai), Tween 80 (Nacalai), Span 20 (Nacalai), Span 85 (Nacalai), CTAB (Nacalai), nonyl-β-D-glucose (Sigma), Adekapluronic L-61 (Asahi Denka Kogyo K.K.; PPG with attached ethylene oxide), Adekanol LG-109 (Asahi Denka Kogyo K.K.; polyether-type PPG), Adekanol LG-294 (Asahi Denka Kogyo K.K.; polyether-type PPG), Adekanol LG-295S (Asahi Denka Kogyo K.K.; polyether-type PPG), Adekanol LG-297 (Asahi Denka Kogyo K.K.; polyether-type PPG), Adekanol B3009A (Asahi Denka Kogyo K.K.; fat or oil/fatty acid ester), and silicone anti-foaming agents KS66 (Shin-Etsu Chemical Co., Ltd.), KS69 (Shin-Etsu Chemical Co., Ltd.), KS502 (Shin-Etsu Chemical Co., Ltd.), KM73 (Shin-Etsu Chemical Co., Ltd.) and KM82F (Shin-Etsu Chemical Co., Ltd.).

For example, a surfactant without anti-foaming activity may be added to a medium at a concentration of 0.005% to 1%, preferably 0.05% to 0.5%. A concentration exceeding 1% is not preferred because such a concentration causes foaming. In contrast, a surfactant with anti-foaming activity can be added at a concentration exceeding 1%.

In the present invention, examples of a terpene include squalene, tocopherol and the like. For example, it may be added to a medium at a concentration of 0.01% or more, preferably 1% or more. Since a concentration exceeding 3% gives no further effect, it is desirable to add a terpene at a concentration of 0.01% to 3% in view of cost.

Among these additives stated above, it is preferable to use a fat or oil, more preferably in combination with a surfactant (particularly, an anti-foaming surfactant), in order to improve prenyl alcohol production and stimulate product secretion from the cells.

In the present invention, prenyl alcohol may be produced in a batch manner or in a continuous manner using a bioreactor. Microorganism cells may be provided as such for prenyl alcohol production or may be pre-treated to give crushed cells, a culture solution, a crude enzyme, or a purified enzyme. Cultured cells or these pre-treated products may also be immobilized by an immobilization technique. The cells or pre-treated products are cultured to produce and accumulate prenyl alcohol in the cells or culture supernatant, which is then collected.

To collect prenyl alcohol from a culture supernatant fraction, a supernatant from which cells have been removed by centrifugation is treated with alkaline phosphatase in a buffer containing magnesium chloride, and then extracted with a solvent such as pentane or methanol.

To collect prenyl alcohol from a cultured cell fraction, on the other hand, the cells collected by centrifugation are crushed, treated with alkaline phosphatase in a buffer containing magnesium chloride, and then extracted with a solvent such as pentane or methanol.

The above solvent extraction step may be performed in combination with a known purification technique such as chromatography, as needed.

The use of alkaline phosphatase in the extraction step is effective in improving farnesol and geranylgeraniol production because it allows hydrolysis of farnesyl pyrophosphate and geranylgeranyl pyrophosphate present as precursors for farnesol and geranylgeraniol in the cells or culture solution. A preferred phosphatase is alkaline phosphatase derived from *E. coli*, but other phosphatases including potato-derived acid phosphatase or calf intestine phosphatase may also be used. Since most microorganisms possess an endogenous phosphatase, the organic solvent extraction step may also be performed without phosphatase treatment, although a slight decrease in production is observed.

In the production method of the present invention, prenyl alcohol is detected by gas chromatography/mass spectrometry (GC/MS) using a commercially available column and then quantified from the ratio of peak area between prenyl alcohol and 1-undecanol as an internal standard.

EXAMPLES

The present invention will be further described in the following examples. The examples are provided for illustrative purposes only, and are not intended to limit the scope of the invention.

Reference Example
(1) Preparation of Liquid Medium

In each of the following examples, yeast cells were cultured in YM medium (Difco) or KY medium prepared as presented below. In particular, squalene synthase-defective yeast cells were cultured in YM medium supplemented with ergosterol.

Bacterial cells or actinomycete cells were cultured in KB medium. A plate was prepared from the same medium by addition of Bactoagar (Difco) at a final concentration of 2%.

YM Medium Supplemented with Ergosterol 20 mg of ergosterol (Sigma) was suspended in an ethanol solution containing 50% Tergitol (Nacalai) and completely dissolved by heating in a boiling water bath. The resulting solution was added to 1 L of YM broth (Difco), followed by autoclaving.

KY Medium

The following ingredients were added to 1 L of deionized water, adjusted to pH 5.5 with 2N sodium hydroxide, and then adjusted to 1 L with deionized water, followed by autoclaving.

| Malt Extract (Difco) | 5 g |
|---|---|
| Yeast Extract (Difco) | 5 g |

KB Medium

The following ingredients were added to 1 L of deionized water, adjusted to pH 7.0 with 2N potassium hydroxide, and then adjusted to 1 L with deionized water, followed by autoclaving.

| Bactotryptone (Difco) | 5 g |
|---|---|
| Yeast Extract (Difco) | 5 g |
| Glucose (Nacalai) | 1 g |
| $KH_2PO_4$ (Nacalai) | 0.7 g |
| $K_2HPO_4$ (Nacalai) | 0.3 g |

(2) Extraction of Prenyl Alcohol from Supernatant Fraction 2.5 ml of the culture solution was transferred into a test tube ($\phi$18 mm×125 mm), and centrifuged in a Beckman centrifuge GP at 1000 rpm for 5 minutes to give the supernatant, which was then transferred to another new test tube ($\phi$18mm×125 mm). 0.5 ml of Tris-HCl buffer (pH 8.0) containing 6 mM magnesium chloride and 5 $\mu$l (2 units) of E. coli alkaline phosphatase (Takara Shuzo Co., Ltd.) were added to the supernatant and heated to 65° C. for 30 minutes. After sufficiently cooling on ice, the treated supernatant was mixed well with 2 ml of pentane and 1 ml of methanol, and centrifuged in a Beckman centrifuge GP at 1000 rpm for 5 minutes to give the supernatant, which was then transferred to another new test tube. After evaporation of pentane and methanol in a draft chamber, the resulting residue was re-dissolved in 300 ml of pentane and filled into a vial for GC/MS.

(3) Extraction of Prenyl Alcohol from Cell Fraction
(i) Extraction from Bacterial and Actinomycete Cells 10 ml of the liquid culture solution was transferred into a 50 ml Corning tube and centrifuged in a Beckman refrigerated centrifuge (Avant J25-I) at 6000 rpm for 5 minutes to collect the cells. After the cells were suspended in 0.5 ml of deionized water, the suspension was transferred into a 10 ml conical bottom tube and crushed using an ultrasonic vibrator UC W-201 (Tokai electric Inc.) at 10° C. for 20 minutes by repeating the following cycle: crushing for 1 minute and allowing to rest for 30 seconds. The crushed cells were transferred into a test tube ($\phi$18 mm×125 mm) and mixed with 0.5 ml of Tris-HCl buffer (pH 8.0) containing 6 mM magnesium chloride, followed by phosphatase treatment and extraction as in (2) above.

(ii) Extraction from Yeast Cells 2.5 ml of the liquid culture solution was transferred into a test tube ($\phi$18 mm×125 mm) and centrifuged in a Beckman centrifuge GP at 1000 rpm for 5 minutes to collect the cells. After the cells were suspended in 0.5 ml of Tris-HCl buffer (pH 8.0) containing 6 mM magnesium chloride, the suspension was transferred into a glass tube for crushing. An equal volume of glass beads (Sigma; acid washed $\phi$=425–600 $\mu$m) was added to the tube and the cells were crushed using a Multi-Beads Shocker MB-200 (YASUI KIKAI) at 2500 rpm and at room temperature for 20 minutes. The whole content of the glass tube was transferred into a test tube ($\phi$18 mm×125 mm), followed by phosphatase treatment and extraction as in (2) above.

(4) Analysis of Prenyl Alcohol

Analysis was performed using a Agilent HP6890/5973 GC/MS system under the following conditions:

| | |
|---|---|
| i) Inlet temperature: | 250° C. |
| ii) Detector temperature: | 260° C. |
| iii) MS zone temperatures: | |
| MS Quad: | 150° C. |
| MS Source: | 230° C. |
| iv) Scan parameters: | |
| Low Mass: | 35 |
| High Mass: | 200 |
| Threshold: | 40 |
| v) Injection parameters: | |
| Mode: | automatic injection |
| Sample volume: | 2 $\mu$l |
| Washing: | 3 times with methanol and twice with hexane |
| Split ratio: | 1:20 |
| Column: | Agilent HP-5MS (0.25 mm × 30 m; film thickness of 0.25 $\mu$m) |
| Carrier gas: | helium at 1.0 ml/min |
| Solvent delay: | 2 minutes |
| Oven conditions: | holding at 115° C. for 1.5 minutes heating to 250° C. at 70° C./min, holding for 2 minutes heating to 300° C. at 70° C./min, holding for 7 minutes post time = 0 |
| Internal standard: | 1-undecanol/ethanol solution (1 $\mu$l/ml), added to each vial in an amount of 10 $\mu$l |
| Inlet liner: | split/splitless liners |
| Analysis: | After incorporation of TIC, 69 mass was selected to integrate the peak area for each of 1-undecanol (RT = 3.39 min), nerolidol (RT = 3.86 min), farnesol |

-continued (RT = 4.23 min) and geranylgeraniol (RT = 5.78 min). Each substance was quantified from the ratio of peak area between the substance and undecanol as an internal standard.

Example 1

Effects of Surfactants on Prenyl Alcohol Secretory Production (1) Strain

Colony selection was performed on squalene synthase-defective yeast strain ATCC#64031 (purchased from ATCC) to select a colony giving an increased farnesol production, which was used in this example.

(2) Preparation of Medium

The above YM medium supplemented with ergosterol was mixed individually with the following surfactants and then autoclaved.

Surfactants:

Tergitol NP-40 (Nacalai)

Triton X-100 (Nacalai)

Tween 20 (Nacalai)

Adekanol LG-109 (Asahi Denka Kogyo K.K.)

Adekapluronic L-61 (Asahi Denka Kogyo K.K.)

Triton X-305 (Nacalai)

Adekanol LG-295S (Asahi Denka Kogyo K.K.)

Adekanol LG-297 (Asahi Denka Kogyo K.K.)

Span 85 (Nacalai)

Adekanol B3009A (Asahi Denka Kogyo K.K.)

(3) Liquid Culture

A loopful of the colony was inoculated from the slant into a 300 ml Erlenmeyer flask containing 50 ml of YM medium supplemented with ergosterol and then cultured at 26° C. while rotating at 150 rpm. After culturing for two days, 50 $\mu$l of the culture was added to 5 ml of the medium prepared in (2) above, followed by shaking culture in a test tube ($\phi$18 mm×150 mm) at 26° C. for two days.

(4) Determination of Cell Counts

100 $\mu$l of the culture solution was diluted with physiological saline to determine its O.D. at 660 nm with a spectrophotometer.

(5) Extraction and Analysis of Prenyl Alcohol from Supernatant Fraction

Extraction and analysis were performed according to the procedures presented in the Reference Example.

(6) Results

FIG. 1 shows effects of Tergitol on the secretory production of geranylgeraniol and farnesol. Tergitol provides an increased farnesol secretion when used at a concentration greater than a normal concentration (0.05%) for dispersing ergosterol in YM medium. Farnesol secretion per cell (O.D. at 660 nm) also shows a similar tendency. This suggests that the secretion of farnesol from the cells gives an improvement in productivity per se, rather than merely allowing farnesol accumulated in the cells to be released from the cells. In contrast, Tergitol also provides an increased geranylgeraniol secretion, but gives little change in productivity per se.

Figure 2:
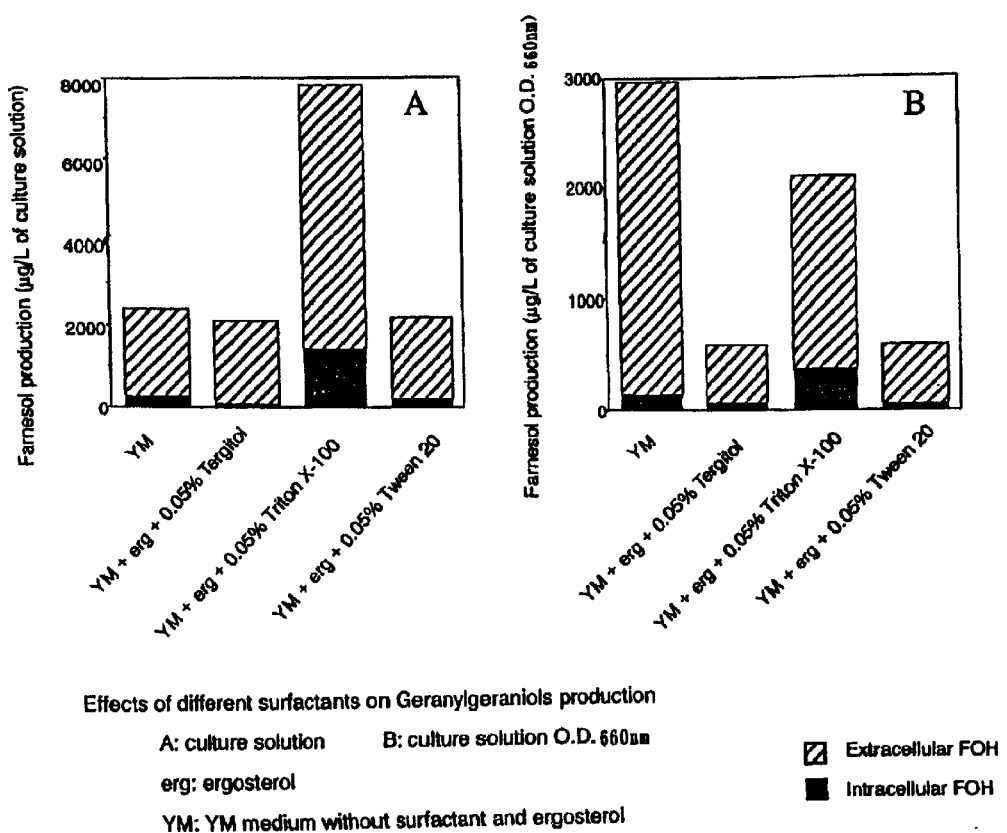
FIG. 2 shows effects of different surfactants on farnesol secretory production (A: culture solution; B: culture solution O.D.).

FIG. 2 shows a comparison between Triton X-100 or Tween 20 and Tergitol. These surfactants also yield similar results. In particular, Triton X-100 has a good ability to dissolve ergosterol, thereby resulting in a significantly increased farnesol production.

Figure 3:
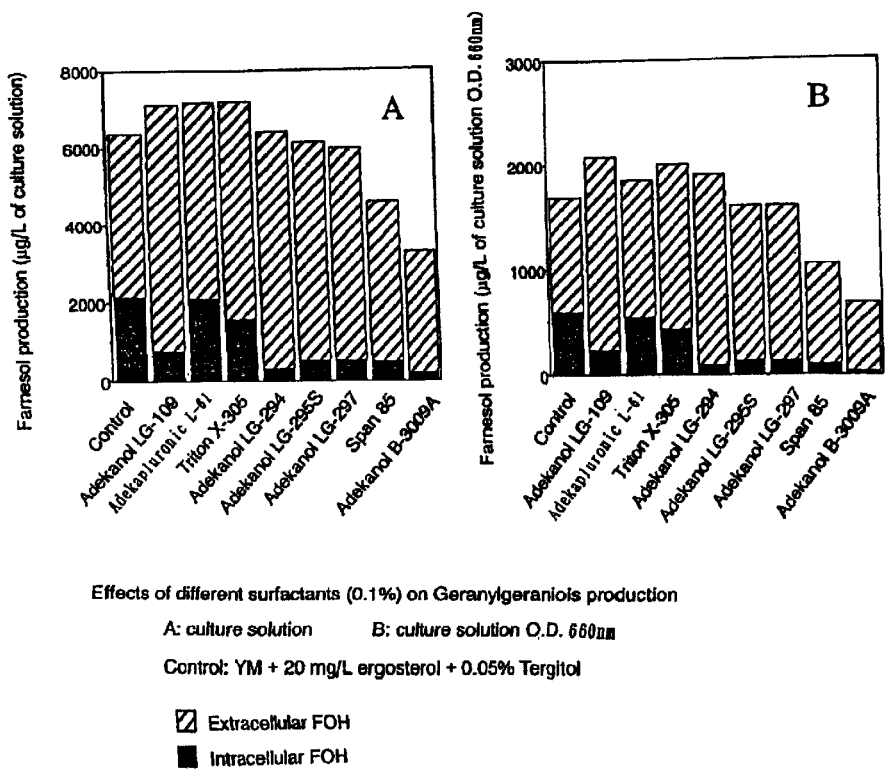
FIG. 3 shows effects of different surfactants on farnesol secretory production (A: culture solution; B: culture solution O.D.).

FIG. 3 shows effects of different anti-foaming agents on farnesol secretion. Several types of anti-forming agents, which had been selected as surfactants enabling jar culture with less foaming and imparting little influence on yeast growth, were used for fermentation and examined for their effects on farnesol secretion in the same manner. With minor differences, all of the examined anti-foaming agents provide almost the same secretion-stimulating effect as Tergitol. These agents are very practical for use because they are safer than non-ionic surfactants commonly used in laboratories, such as Triton X-100, and also have an anti-foaming activity.

Figure 4:
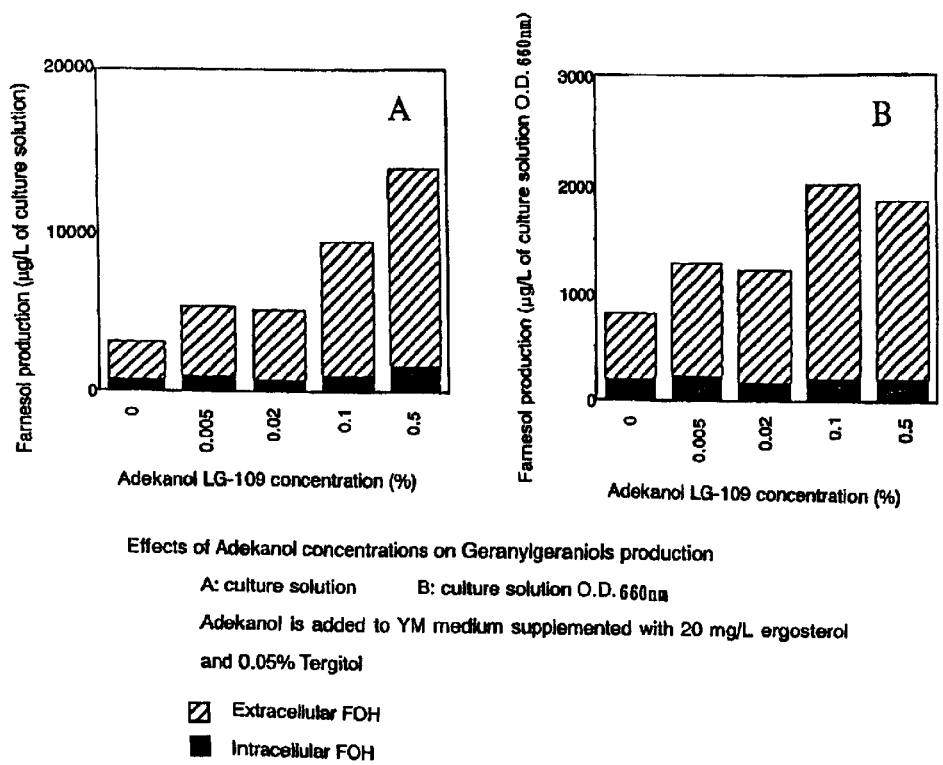
FIG. 4 shows effects of different surfactant concentrations on farnesol secretory production (A: culture solution; B: culture solution O.D.).

FIG. 4 shows the test results obtained at various concentrations of Adekanol LG-109, which yielded a good result in FIG. 3. When used at a concentration of 0% to 0.5%, Adekanol LG-109 provided an increased farnesol secretion as its concentration was increased.

Example 2

Effects of Fats or Oils on Prenyl Alcohol Secretory Production

A medium prepared by adding a fat or oil (almond oil, fish oil, soybean oil, or olive oil; each commercially available from Sigma), at a final concentration of 0.1%, to the YM medium supplemented with ergosterol stated above was used for culture of the squalene synthase-defective yeast strain (ATCC#64031) to examine an effect of the fat or oil on farnesol secretory production in the same manner as described in Example 1.

Figure 5:
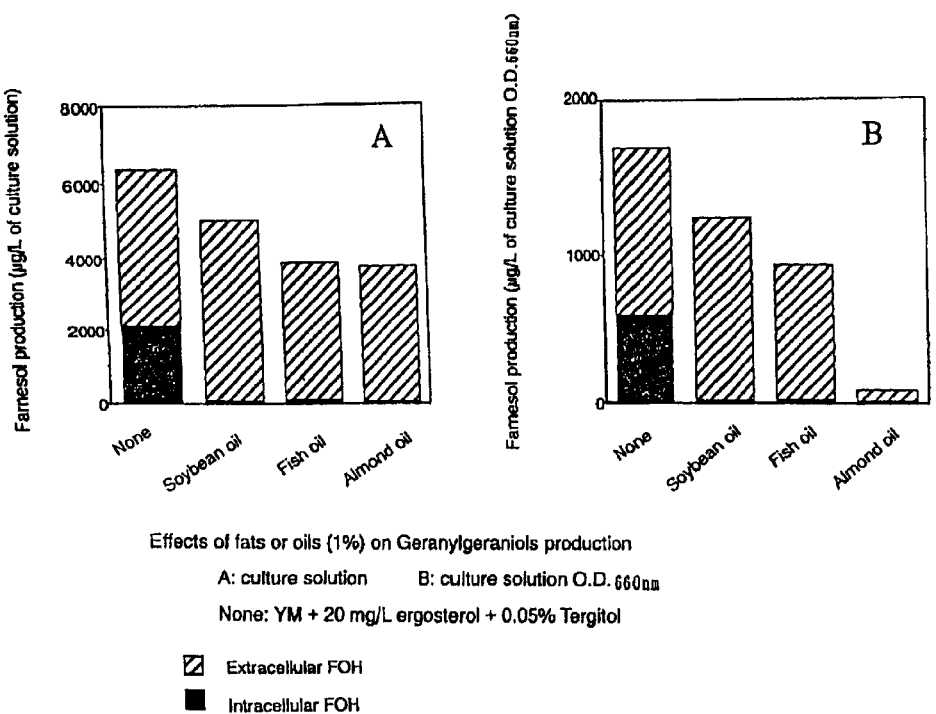
FIG. 5 shows effects of fats or oils on farnesol secretory production (A: culture solution; B: culture solution O.D.).

FIG. 5 shows the results of culture in a medium containing almond oil, fish oil or soybean oil. Each system contains 0.05% Tergitol as a dispersant for the purpose of incorporating ergosterol required for culture of the strain into the medium. For this reason, even a system without a fat or oil allows about two-thirds secretion of farnesol from the cells. In contrast, each system containing a fat or oil results in 98% or more farnesol secretion.

Figure 6:
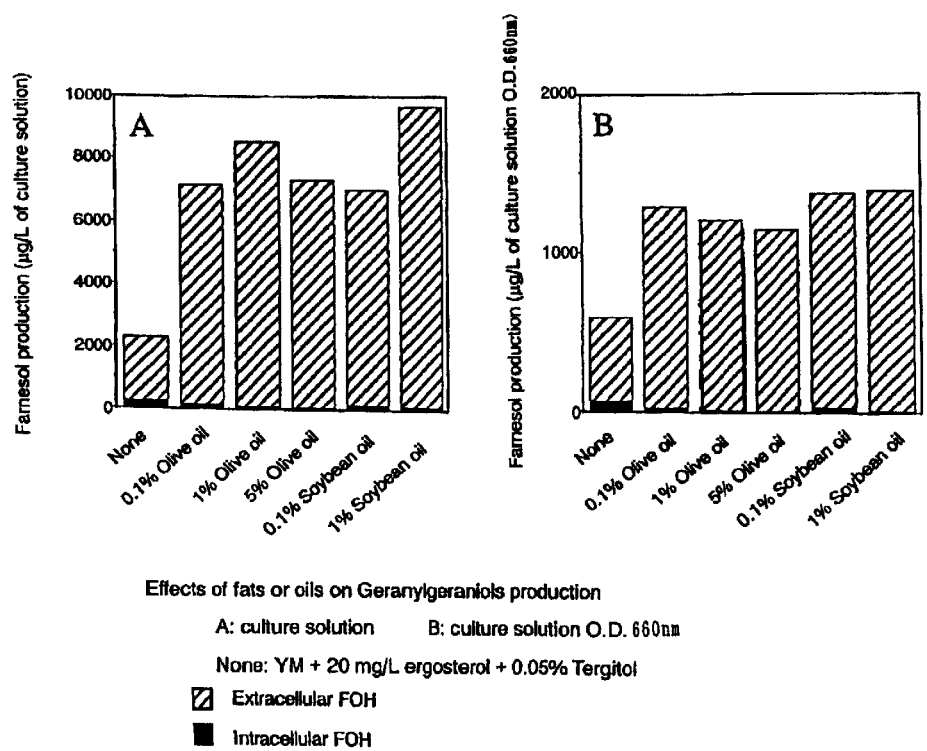
FIG. 6 shows effects of fat or oil concentrations on farnesol secretory production (A: culture solution; B: culture solution O.D.).

FIG. 6 shows the results of similar tests performed under increasing concentrations of soybean oil and olive oil.

Each system containing the above fat or oil provides not only an increased farnesol secretion, but also an increased farnesol production as the concentration of fat or oil is increased.

Thus, the addition of a fat or oil was also shown to give a farnesol secretion-stimulating effect as in the case of a surfactant.

Example 3

Effects of Sugars on Prenyl Alcohol Secretory Production

A medium prepared by adding a sugar (glucose or sucrose; each commercially available from Nacalai) to the YM medium supplemented with ergosterol stated above was used for culture of the squalene synthase-defective yeast strain (ATCC#64031) to examine an effect of the sugar on farnesol secretory production in the same manner as described in Example 1.

Since YM medium (Difco) originally contains 1% glucose, the final sugar concentration is expressed as 1% glucose plus additional glucose or sucrose (0% to 5%).

Figure 7:
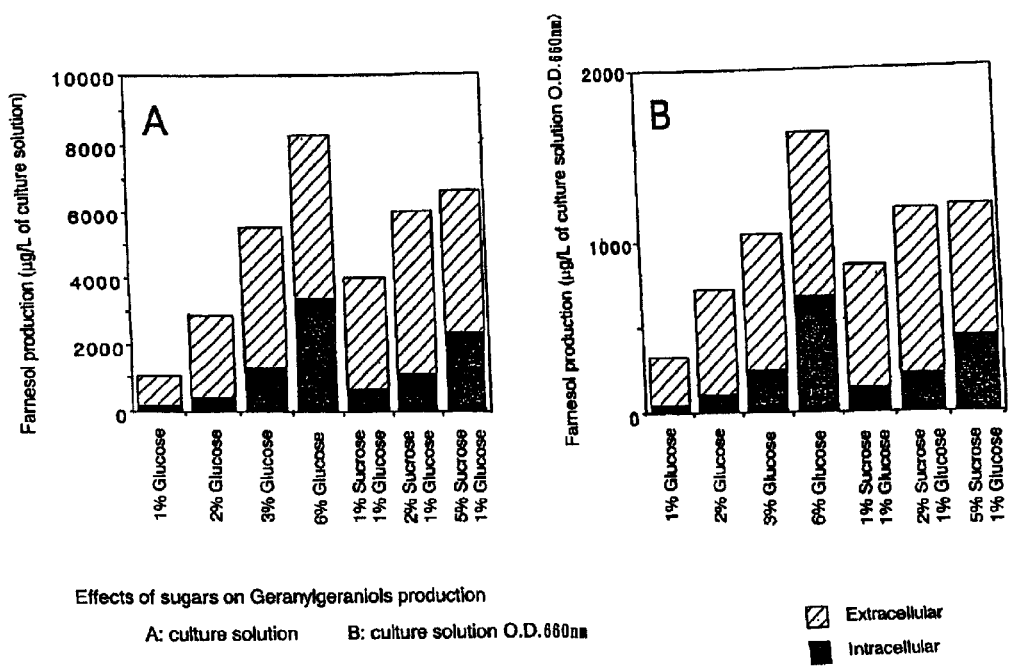
FIG. 7 shows effects of sugar concentrations on farnesol secretory production (A: culture solution; B: culture solution O.D.).

FIG. 7 shows the results of culture in a medium containing glucose or sucrose at different concentrations. This figure indicates that a higher sugar concentration tends to give a higher production of farnesol. A higher production results in an increased amount of farnesol accumulated in the cells, but farnesol secretion is not significantly increased, thereby suggesting that secretion speed is not as fast as production speed.

Farnesol secretory production per cell (O.D. at 660 nm) also shows a similar tendency, and therefore an increased sugar concentration in the medium results in an increased farnesol production per cell.

Example 4

Combined Effects of Sugars, Fats or Oils, and Surfactants on Prenyl Alcohol Secretory Production A medium prepared by adding 6% glucose as a sugar, 1% soybean oil as a fat or oil, and/or 0.1% Triton X-100 as a surfactant, alone or in combination, to the YM medium supplemented with ergosterol stated above was used for culture of the squalene synthase-defective yeast strain (ATCC#64031) to examine effects of these ingredients on geranylgeraniol and farnesol secretory production in the same manner as described in Example 1.

Figure 8:
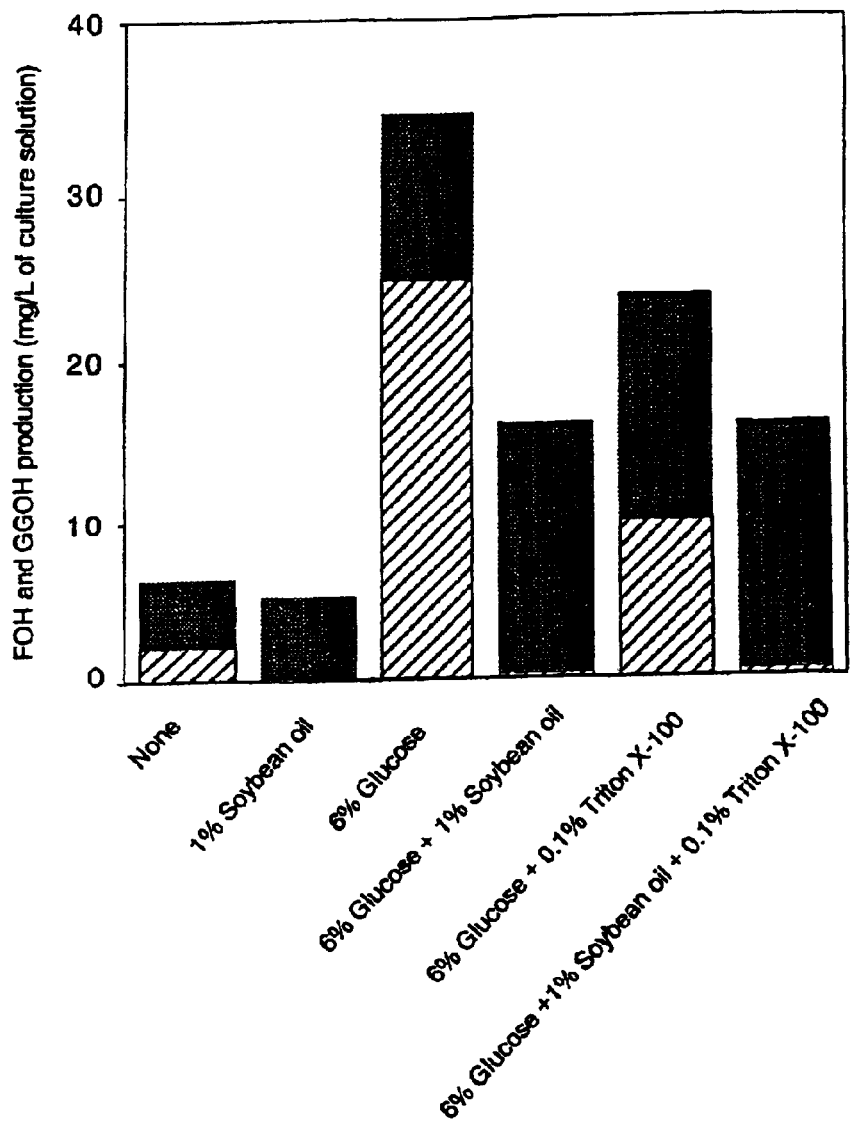
FIG. 8 shows effects of a sugar, a fat or oil, a surfactant and combinations thereof on geranylgeraniol and farnesol secretory production.

FIG. 8 shows the results obtained. When 1% soybean oil is added, farnesol in the cells is significantly decreased, and farnesol secretion is increased. When 6% glucose is added, farnesol production in the cells is primarily increased. In a system containing 6% glucose and 1% soybean oil, farnesol secretion is increased and the cells are therefore found to contain little farnesol. Such an effect is also seen in a system containing 6% glucose and 0.1% Triton X-100, but Triton X-100 has a minor effect on farnesol secretion as compared with soybean oil. Further, a system containing 6% glucose, 1% soybean oil and 0.1% Triton X-100 shows almost the same secretion effect and production as the system containing glucose and soybean oil.

In contrast, geranylgeraniol is not detected in a cell fraction at all. Only the system containing glucose and soybean oil or Triton X-100 allows geranylgeraniol to be secreted from the cells. This indicates that the addition of these ingredients also stimulates geranylgeraniol secretion, thereby resulting in an increased production.

Figure 9:
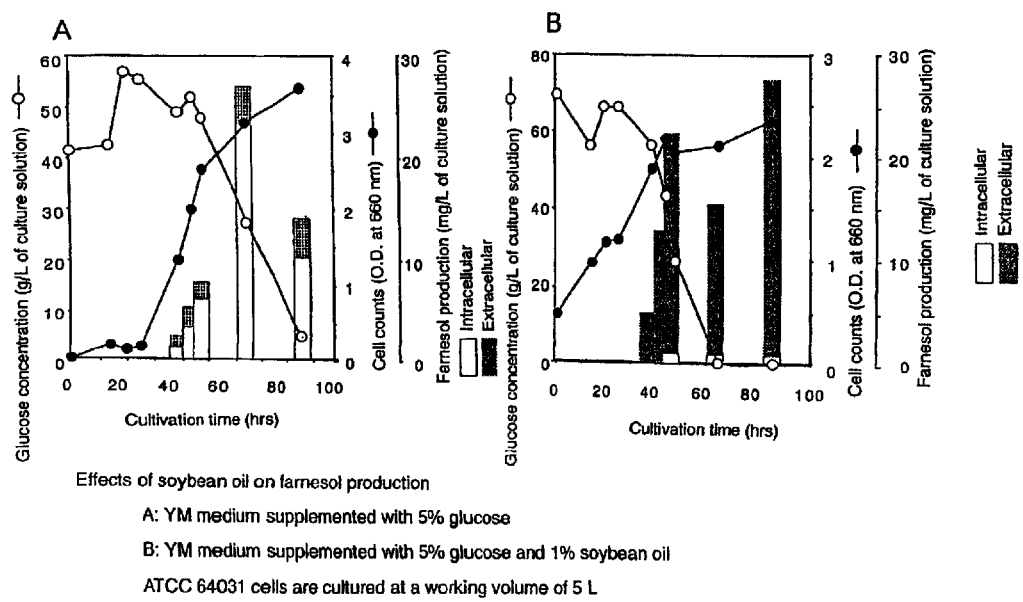
FIG. 9 shows combined effects of a sugar and a fat or oil on farnesol secretory production.

FIG. 9 shows effects of soybean oil on farnesol secretion in jar-fermenter culture. FIG. 9(A) shows a culture profile of a system containing 5% glucose. This figure indicates a stage where a maximum concentration of farnesol accumulated in the medium is observed, thereby suggesting that farnesol is predominantly accumulated in the cells. This is because farnesol present in the cells is metabolized when glucose is depleted. In contrast, FIG. 9(B) shows a culture profile of a system containing 5% glucose and 1% soybean oil. This system shows an increased farnesol production as compared with the system containing 5% glucose alone, and hence allows 95% or more farnesol to be secreted from the cells. Since no decrease in farnesol production is observed even at the late stage of culture, it is believed that farnesol dissolves into soybean oil, thereby avoiding metabolism, which results in an increased farnesol production. When compared with FIGS. 1 to 8, FIG. 9(A) shows less secretion in the system without a fat or oil. This is because the ergosterol concentration in the medium is reduced to 4 mg/L in this system, and therefore the concentration of Tergitol, a dispersant for ergosterol, is reduced to one-fifth, i.e., 0.01%.

Example 5

Effects of Tocopherol and Squalene on Prenyl Alcohol Secretory Production

A medium prepared by adding tocopherol or squalene at a concentration shown in Tables 1 and 2 to the YM medium supplemented with ergosterol stated above was used for culture of *Saccharomyces cerevisiae* strains ATCC 64031 and IFO 0538 to examine an effect of tocopherol or squalene on prenyl alcohol secretory production. Tables 1 and 2 also show the results obtained. *Saccharomyces cerevisiae* strain IFO 0538 is found to produce no prenyl alcohol in YM medium commonly used for yeast culture. However, this strain enables prenyl alcohol production in the presence of squalene, and geranylgeraniol and farnesol are found in the supernatant at a higher concentration than that found in the cells (Table 2). Table 1 shows the results obtained using *Saccharomyces cerevisiae* strain ATCC 64031 which inherently produces farnesol. This strain produces more farnesol in the supernatant fraction as the concentration of tocopherol is increased.

TABLE 1

| Tocopherol concentration ($\mu$M) | Supernatant fraction ($\mu$g/L of culture solution) | | | Cell fraction ($\mu$g/L of culture solution) | | |
|---|---|---|---|---|---|---|
| | DHFOH | FAL | FOH | DHFOH | FAL | FOH |
| 0 | 1238 | 84 | 3102 | 4630 | 217 | 7034 |
| 20 | 1573 | 84 | 3819 | 3622 | 179 | 5469 |
| 200 | 3527 | 120 | 6741 | 2206 | 127 | 2695 |

Strain used: *Saccharomyces cerevisiae* strain ATCC 64031
DHFOH: dehydrofarnesol
FOH: farnesol
FAL: farnesal

TABLE 2

| Squalene (%) | Soybean oil (%) | Days | Supernatant fraction ($\mu$g/L of culture solution) | | | Cell fraction ($\mu$g/L of culture solution) | | |
|---|---|---|---|---|---|---|---|---|
| | | | NE | FOH | GGOH | NE | FOH | GGOH |
| 0 | 0 | 3 | 0.0 | 0.0 | 0.0 | 0.0 | 0.0 | 0.0 |
| | | 7 | 0.0 | 0.0 | 0.0 | 0.0 | 0.0 | 0.0 |
| 0 | 1 | 3 | 0.0 | 71.5 | 22.8 | 0.0 | 17.1 | 21.0 |
| | | 7 | 0.0 | 56.2 | 67.6 | 0.0 | 9.2 | 27.9 |
| 1 | 0 | 3 | 0.0 | 204.8 | 0.0 | 0.0 | 30.4 | 120.2 |
| | | 7 | 0.0 | 109.8 | 133.9 | 0.0 | 4.7 | 0.0 |
| 0.5 | 0.5 | 3 | 0.0 | 150.5 | 90.4 | 0.0 | 19.4 | 264.6 |
| | | 7 | 0.0 | 58.1 | 287.8 | 0.0 | 0.0 | 179.1 |

Strain used: *Saccharomyces cerevisiae* strain IFO 0538
NE: nerolidol
FOH: farnesol
GGOH: geranylgeraniol Example 6

Combined Sugars and Fats or Oils on Prenyl Alcohol Secretory Production

*Hanseniaspora valbyensis* strain IFO 0115, *Saccharomycodes ludwigii* strain IFO 0339 and *Candida glabrata* strain IFO 0005, all of which inherently provide high production of farnesol and geranylgeraniol without addition of a specific ingredient to a medium, were separately cultured in an Erlenmeyer flask. The results, including days of culture, medium composition, and changes in production with or without phosphatase treatment, are shown in Table 3 (supernatant fraction) and Table 4 (cell fraction). Each strain produces more farnesol and geranylgeraniol over the course of time. The addition of 5% glucose to the medium permits an increased production in the cells. The addition of 1% soybean oil along with glucose stimulated *Candida glabrata* strain to secrete, farnesol and geranylgeraniol from the cells.

In contrast, *Hanseniaspora valbyensis* strain IFO 0115 and *Saccharomycodes ludwigii* strain IFO 0339 showed no secretion-stimulating effect attributed to soybean oil in this example. This is because uniform sampling of farnesol and geranylgeraniol was difficult due to phase separation between the oil phase with a high product content and the aqueous phase with a low product content. However, each of these strains was cultured in a test tube for full volume analysis, indicating that these two strains showed the same secretion-stimulating effects (Tables 9 to 11).

Thus, although some differences are found among microorganisms, the use of the medium supplemented with 5% glucose and 1% soybean oil enables more farnesol and geranylgeraniol to be produced in both the cell fraction and the supernatant fraction (i.e., to be secreted from the cells).

Also, the supernatant fraction tends to contain more farnesol and geranylgeraniol in the absence of phosphatase treatment, whereas the cell fraction tends to contain more farnesol and geranylgeraniol when treated with phosphatase, thereby suggesting that farnesyl pyrophosphate and geranyl pyrophosphate are present in the cell fraction.

TABLE 3

| | | | Supernatant fraction ($\mu$g/L of culture solution) | | | |
|---|---|---|---|---|---|---|
| | | cultivation period | Phosphatase-untreated | | Phosphatase-treated | |
| Strain No. | Medium composition | (day(s)) | FOH | GGOH | FOH | GGOH |
| IFO 0005 *Candida glabrata* | YM | 1 | 0.0 | 0.0 | 1.5 | 0.0 |
| | | 2 | 0.0 | 0.0 | 0.0 | 0.0 |
| | | 3 | 0.0 | 0.0 | 0.0 | 0.0 |
| | YM + Glc | 1 | 0.0 | 0.0 | 6.1 | 0.0 |
| | | 2 | 0.0 | 0.0 | 9.5 | 0.0 |
| | | 3 | 29.4 | 2.3 | 13.9 | 0.0 |
| | YM + Glc + SBO | 1 | 0.0 | 0.0 | 0.0 | 0.0 |
| | | 2 | 135.6 | 92.0 | 69.9 | 31.5 |
| | | 3 | 850.7 | 416.5 | 116.6 | 40.0 |
| IFO 0115 *Hanseniaspora valbyensis* | YM | 1 | 0.0 | 0.0 | 0.0 | 0.0 |
| | | 2 | 0.0 | 0.0 | 0.0 | 0.0 |
| | | 3 | 34.0 | 0.0 | 0.0 | 0.0 |
| | YM + Glc | 1 | 0.0 | 0.0 | 0.0 | 0.0 |
| | | 2 | 11.3 | 0.0 | 0.0 | 0.0 |
| | | 3 | 36.4 | 0.0 | 18.0 | 0.0 |
| | YM + Glc + SBO | 1 | 0.0 | 0.0 | 0.0 | 0.0 |
| | | 2 | 24.0 | 0.0 | 5.1 | 0.0 |
| | | 3 | 30.3 | 26.5 | 7.9 | 0.0 |
| IFO 0339 *Saccharomycodes ludwigii* | YM | 1 | 0.0 | 0.0 | 0.0 | 0.0 |
| | | 2 | 8.7 | 0.0 | 0.0 | 0.0 |
| | | 3 | 0.0 | 0.0 | 0.0 | 0.0 |
| | YM + Glc | 1 | 0.0 | 0.0 | 0.0 | 0.0 |
| | | 2 | 16.8 | 0.0 | 17.7 | 0.0 |
| | | 3 | 67.1 | 0.0 | 20.8 | 0.0 |
| | YM + Glc + SBO | 1 | 0.0 | 0.0 | 0.0 | 0.0 |
| | | 2 | 11.7 | 5.3 | 0.0 | 0.0 |
| | | 3 | 85.6 | 7.3 | 6.5 | 0.0 |

FOH: farnesol
GGOH: geranylgeraniol
YM: YM medium (Difco)
YM + Glc: YM medium (Difco) + 5% glucose
YM + Glc + SBO: YM medium (Difco) + 5% glucose + 1% soybean oil

TABLE 4

| | | | Cell fraction ($\mu$g/L of culture solution) | | | |
|---|---|---|---|---|---|---|
| | | cultivation period | Phosphatase-untreated | | Phosphatase-treated | |
| Strain No. | Medium composition | (day(s)) | FOH | GGOH | FOH | GGOH |
| IFO 0005 *Candida glabrata* | YM | 1 | 39.4 | 0.0 | 0.0 | 0.0 |
| | | 2 | 14.8 | 37.3 | 0.0 | 0.0 |
| | | 3 | 11.4 | 41.7 | 51.2 | 0.0 |
| | YM + Glc | 1 | 8.4 | 0.0 | 0.0 | 0.0 |
| | | 2 | 44.1 | 134.4 | 86.8 | 304.8 |
| | | 3 | 104.4 | 323.9 | 202.4 | 772.6 |
| | YM + Glc + SBO | 1 | 5.8 | 0.0 | 0.0 | 0.0 |
| | | 2 | 427.4 | 178.9 | 248.0 | 239.6 |
| | | 3 | 835.3 | 363.7 | 1321.6 | 1176.2 |

TABLE 4-continued

|  |  |  | Cell fraction (μg/L of culture solution) | | | |
|---|---|---|---|---|---|---|
|  |  | cultivation period | Phosphatase-untreated | | Phosphatase-treated | |
| Strain No. | Medium composition | (day(s)) | FOH | GGOH | FOH | GGOH |
| IFO 0115 | YM | 1 | 0.0 | 0.0 | 0.0 | 0.0 |
| *Hanseniaspora* |  | 2 | 34.0 | 5.1 | 0.0 | 0.0 |
| *valbyensis* |  | 3 | 21.1 | 45.6 | 0.0 | 63.7 |
|  | YM + Glc | 1 | 0.0 | 0.0 | 0.0 | 0.0 |
|  |  | 2 | 46.6 | 26.1 | 23.9 | 0.0 |
|  |  | 3 | 54.2 | 108.5 | 78.0 | 491.8 |
|  | YM + Glc + SBO | 1 | 0.0 | 0.0 | 0.0 | 0.0 |
|  |  | 2 | 0.0 | 0.0 | 9.7 | 0.0 |
|  |  | 3 | 61.3 | 122.0 | 69.2 | 286.1 |
| IFO 0339 | YM | 1 | 18.0 | 0.0 | 0.0 | 0.0 |
| *Saccharomycodes* |  | 2 | 16.6 | 0.0 | 0.0 | 0.0 |
| *ludwigii* |  | 3 | 19.5 | 48.3 | 0.0 | 71.0 |
|  | YM + Glc | 1 | 0.0 | 0.0 | 0.0 | 0.0 |
|  |  | 2 | 58.6 | 34.1 | 12.0 | 0.0 |
|  |  | 3 | 62.3 | 173.8 | 67.8 | 464.8 |
|  | YM + Glc + SBO | 1 | 0.0 | 0.0 | 0.0 | 0.0 |
|  |  | 2 | 96.4 | 10.3 | 9.3 | 0.0 |
|  |  | 3 | 61.6 | 103.7 | 27.9 | 135.6 |

FOH: farnesol
GGOH: geranylgeraniol
YM: YM medium (Difco)
YM + Glc: YM medium (Difco) + 5% glucose
YM + Glc + SBO: YM medium (Difco) + 5% glucose + 1% soybean oil Example 7

Combined Effects of Sugars and Fats or Oils on Prenyl Alcohol Secretory Production Some of the strains shown in Table 5 were test-tube cultured in YM medium alone and in YM medium supplemented with 5% glucose and 1% soybean oil to examine farnesol and geranylgeraniol production. Tables 5 and 6 show the results obtained. The medium supplemented with 5% glucose and 1% soybean oil effected a significantly increased production in both the cell fraction and the supernatant fraction (i.e., a significantly increased secretion from the cells).

TABLE 5

Medium composition: YM medium (Difco)

|  |  | Supernatant fraction | | Cell fraction | |
|---|---|---|---|---|---|
| Strains | | (μg/L of culture solution) | | | |
| Strain No. | Genus | FOH | GGOH | FOH | GGOH |
| K 4104 | *Saccharomyces cerevisiae* | 0.0 | 0.0 | 15.8 | 31.7 |
| IFO 0252 | *Saccharomyces rosei* | 0.0 | 0.0 | 28.5 | 39.0 |
| IFO 0565 | *Saccharomyces cerevisiae* | 0.0 | 0.0 | 0.0 | 54.7 |
| IFO 0941 | *Williopsis saturnus* var. saturnus | 4.7 | 0.0 | 69.8 | 78.7 |
| IFO 1475 | *Ogataea polymorpha* | 0.0 | 0.0 | 13.5 | 36.1 |
| IFO 0648 | *Kluyveromyces lactis* | 6.0 | 0.0 | 6.3 | 72.9 |

K: strain maintained by Kyoto University
FOH: farnesol
GGOH: geranylgeraniol

TABLE 6

Medium composition: YM medium (Difco) + 5% glucose + 1% soybean oil

|  |  |  | Supernatant fraction | | Cell fraction | |
|---|---|---|---|---|---|---|
| Strains | |  Cultivation | (μg/L of culture solution) | | | |
| Strain No. | Genus | days | FOH | GGOH | FOH | GGOH |
| K 4104 | *Saccharomyces cerevisiae* | 3 | 281.0 | 127.7 | 241.1 | 161.6 |
|  |  | 6 | 338.2 | 186.9 | 155.3 | 132.2 |
| IFO 2052 | *Saccharomyces rosei* | 3 | 220.0 | 98.0 | 305.9 | 140.2 |
|  |  | 6 | 381.2 | 176.6 | 193.1 | 122.5 |
| IFO 0565 | *Saccharomyces cerevisiae* | 3 | 49.3 | 16.0 | 88.0 | 78.2 |
|  |  | 6 | 51.9 | 34.1 | 248.5 | 214.2 |
| IFO 0941 | *Williopsis saturnus* var. saturnus | 3 | 54.8 | 22.6 | 255.3 | 169.3 |
|  |  | 6 | 88.3 | 33.1 | 363.2 | 220.9 |

TABLE 6-continued

Medium composition: YM medium (Difco) + 5% glucose + 1% soybean oil

| Strains | | Cultivation | Supernatant fraction ($\mu$g/L of culture solution) | | Cell fraction | |
|---|---|---|---|---|---|---|
| Strain No. | Genus | days | FOH | GGOH | FOH | GGOH |
| IFO 1475 | *Ogataea polymorpha* | 3 | 60.9 | 69.1 | 113.5 | 127.2 |
| | | 6 | 19.8 | 14.4 | 60.8 | 95.9 |
| IFO 0648 | *Kluyveromyces lactis* | 3 | 28.5 | 37.8 | 61.8 | 91.1 |
| | | 6 | 120.3 | 124.5 | 159.8 | 211.5 |

K: strain maintained by Kyoto University
FOH: farnesol
GGOH: geranylgeraniol

Example 8

Combined Effects of Sugars and Fats or Oils on Prenyl Alcohol Secretory Production Each of the strains shown in Tables 7 and 8 below was test-tube cultured in (i) YM medium supplemented with 4 mg/L ergosterol and 0–20 mg/L squalene synthesis inhibitor (SQAD: Japanese Patent Application No. 8-508245) or (ii) YM medium supplemented with 5% glucose and 1% soybean oil along with 4 mg/L ergosterol and 0–20 mg/L squalene synthesis inhibitor (SQAD) to examine the respective production of nerolidol, geranylgeraniol and farnesol in the same manner as stated above. Tables 7 and 8 also show the results obtained.

These tables indicate that the addition of soybean oil, glucose and a squalene synthesis inhibitor effects an increased production in both the cell fraction and the supernatant fraction (i.e., an increased secretion from the cells).

TABLE 7

Medium composition: YM medium (Difco) + 4 mg/L ergosterol + 0–20 mg/L SQAD

| Strain No. | SQAD | Days | Supernatant fraction ($\mu$g/L of culture solution) | | | Cell fraction | | |
|---|---|---|---|---|---|---|---|---|
| | | | NE | FOH | GGOH | NE | FOH | GGOH |
| IFO 0215 | 0 | 3 | 0.0 | 0.0 | 0.0 | 0.0 | 0.0 | 0.0 |
| *Saccharomyces unisporus* | 1 | | 0.0 | 0.0 | 0.0 | 0.0 | 0.0 | 0.0 |
| | 20 | | 0.0 | 3.2 | 0.0 | 0.0 | 0.0 | 0.0 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0538 | 0 | 3 | 0.0 | 0.0 | 0.0 | 0.0 | 0.0 | 0.0 |
| *Saccharomyces cerevisiae* | 1 | | 0.0 | 0.0 | 0.0 | 0.0 | 0.0 | 0.0 |
| | 20 | | 0.0 | 0.0 | 0.0 | 0.0 | 8.1 | 0.0 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0622 | 0 | 3 | 0.0 | 3.1 | 0.0 | 0.0 | 1.9 | 30.4 |
| *Candida glabrata* | 1 | | 0.0 | 3.5 | 0.0 | 0.0 | 1.4 | 24.3 |
| | 20 | | 0.0 | 243.5 | 0.0 | 0.0 | 212.0 | 57.0 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 5.5 | 40.5 |
| IFO 0717 | 0 | 3 | 0.0 | 0.0 | 0.0 | 0.0 | 0.0 | 0.0 |
| *Yarrowia lipolytica* | 1 | | 0.0 | 1.3 | 0.0 | 0.0 | 0.0 | 0.0 |
| | 20 | | 0.0 | 39.7 | 66.5 | 0.0 | 39.7 | 63.5 |
| | 0 | 7 | 0.0 | 0.0 | 0.0 | 0.0 | 0.0 | 0.0 |
| | 1 | | 0.0 | 2.1 | 0.0 | 0.0 | 1.5 | 0.0 |
| | 20 | | 0.0 | 10.6 | 0.0 | 0.0 | 10.6 | 0.0 |
| IFO 0948 | 0 | 3 | 0.0 | 0.0 | 0.0 | 0.0 | 0.0 | 0.0 |
| *Komagataella pastoris* | 1 | | 0.0 | 0.0 | 0.0 | 0.0 | 0.0 | 0.0 |
| | 20 | | 0.0 | 3.4 | 2.3 | 0.0 | 3.4 | 1.8 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0974 | 0 | 3 | 0.0 | 0.0 | 0.0 | 0.0 | 0.0 | 0.0 |
| *Kuraishia capsulata* | 1 | | 0.0 | 0.0 | 0.0 | 0.0 | 0.0 | 0.0 |
| | 20 | | 0.0 | 0.0 | 0.0 | 0.0 | 0.0 | 0.0 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |

TABLE 7-continued

Medium composition: YM medium (Difco) + 4 mg/L ergosterol + 0–20 mg/L SQAD

| | | | Supernatant fraction | | | Cell fraction | | |
|---|---|---|---|---|---|---|---|---|
| | | | ($\mu$g/L of culture solution) | | | | | |
| Strain No. | SQAD | Days | NE | FOH | GGOH | NE | FOH | GGOH |
| IFO 1472 | 0 | 3 | 0.0 | 0.0 | 0.0 | 0.0 | 0.0 | 0.0 |
| Ogataea glucozyma | 1 | | 0.0 | 0.0 | 0.0 | 0.0 | 0.0 | 0.0 |
| | 20 | | 0.0 | 0.0 | 18.3 | 0.0 | 0.0 | 17.5 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 6.8 |
| IFO 1892 | 0 | 3 | 0.0 | 0.0 | 0.0 | 0.0 | 0.0 | 8.9 |
| Saccharomyces kluyeri | 1 | | 0.0 | 0.0 | 0.0 | 0.0 | 0.0 | 16.7 |
| | 20 | | 0.0 | 0.0 | 0.0. | 0.0 | 0.0 | 38.5 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 1910 | 0 | 3 | 0.0 | 0.0 | 0.0 | 0.0 | 0.0 | 0.0 |
| Candida cariosilignicola | 1 | | 0.0 | 0.0 | 0.0 | 0.0 | 0.0 | 0.0 |
| | 20 | | 0.0 | 0.0 | 0.0 | 0.0 | 0.0 | 5.5 |
| | 0 | 7 | 0.0 | 0.0 | 0.0 | 0.0 | 0.0 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |
| IFO 0005 | 0 | 3 | 0.0 | 0.0 | 0.0 | 0.0 | 0.0 | 12.0 |
| Candia glabrata | 1 | | 0.0 | 0.0 | 0.0 | 0.0 | 0.0 | 4.3 |
| | 20 | | 0.0 | 33.8 | 2.7 | 0.0 | 0.0 | 53.7 |
| | 0 | 7 | 0.0 | 0.0 | 0.0 | 0.0 | 20.5 | 0.0 |
| | 1 | | 0.0 | 0.0 | 0.0 | 0.0 | 0.0 | 0.0 |
| | 20 | | 0.0 | 0.0 | 0.0 | 0.0 | 0.0 | 0.0 |

NE: nerolidol
FOH: farnesol
GGOH: geranylgeraniol
SQAD: squalene synthesis inhibitor 0; none 1; 1 mg/L 20; 20 mg/L

TABLE 8

Medium composition: YM medium (Difco) + 5% glucose + 1% soybean oil 4 mg/L ergosterol + 0–20 mg/L SQAD

| | | | Supernatant fraction | | | Cell fraction | | |
|---|---|---|---|---|---|---|---|---|
| | | | ($\mu$g/L of culture solution) | | | | | |
| Strain No. | SQAD | Days | NE | FOH | GGOH | NE | FOH | GGOH |
| IFO 0215 | 0 | 3 | 16.3 | 8.2 | 0.0 | 0.0 | 0.0 | 0.0 |
| Saccharomyces | 1 | | 12.2 | 5.2 | 0.0 | 0.0 | 0.0 | 0.0 |
| unisporus | 20 | | 67.4 | 68.4 | 0.0 | 0.0 | 16.9 | 0.0 |
| | 0 | 7 | 19.6 | 14.8 | 0.0 | 0.0 | 0.0 | 0.0 |
| | 1 | | 27.3 | 17.5 | 0.0 | 0.0 | 0.0 | 0.0 |
| | 20 | | 466.6 | 433.7 | 21.6 | 8.6 | 255.6 | 0.0 |
| IFO 0538 | 0 | 3 | 0.0 | 139.3 | 59.8 | 0.0 | 0.0 | 0.0 |
| Saccharomyces | 1 | | 0.0 | 102.9 | 46.2 | 0.0 | 15.5 | 0.0 |
| cerevisiae | 20 | | 65.9 | 9087.5 | 331.6 | 0.0 | 1465.9 | 51.0 |
| | 0 | 7 | 0.0 | 426.4 | 246.7 | 0.0 | 38.0 | 0.0 |
| | 1 | | 0.0 | 319.5 | 241.0 | 0.0 | 188.8 | 85.6 |
| | 20 | | 216.2 | 34241.4 | 1568.8 | 18.4 | 5812.1 | 266.2 |
| IFO 0622 | 0 | 3 | 0.0 | 106.1 | 112.3 | 0.0 | 28.8 | 33.6 |
| Candida | 1 | | 9.4 | 149.2 | 119.7 | 0.0 | 9.7 | 0.0 |
| glabrata | 20 | | 422.2 | 12186.9 | 327.2 | 0.0 | 331.6 | 9.3 |
| | 0 | 7 | 11.6 | 378.3 | 408.5 | 0.0 | 43.7 | 59.2 |
| | 1 | | 17.2 | 530.0 | 231.5 | 0.0 | 133.3 | 58.5 |
| | 20 | | 1256.9 | 22147.1 | 862.7 | 138.0 | 2750.6 | 170.5 |
| IFO 0717 | 0 | 3 | 0.0 | 8.7 | 0.0 | 0.0 | 6.7 | 0.0 |
| Yarrowia | 1 | | 2.4 | 100.1 | 19.1 | 0.0 | 165.3 | 0.0 |
| lopolytica | 20 | | 19.0 | 983.3 | 17.8 | 0.0 | 882.1 | 0.0 |
| | 0 | 7 | 0.0 | 95.3 | 608.0 | 0.0 | 0.0 | 38.4 |
| | 1 | | 19.0 | 405.4 | 546.8 | 0.0 | 0.0 | 0.0 |
| | 20 | | 156.7 | 6812.9 | 76.2 | 0.0 | 1025.1 | 41.8 |
| IFO 0948 | 0 | 3 | 0.0 | 73.5 | 78.9 | 0.0 | 13.8 | 42.3 |
| Komagataella | 1 | | 0.0 | 82.2 | 71.5 | 0.0 | 22.9 | 28.4 |
| pastoris | 20 | | 17.2 | 2956.2 | 132.5 | 0.0 | 608.4 | 80.1 |
| | 0 | 7 | 0.0 | 101.6 | 83.5 | 0.0 | 4.3 | 11.0 |

TABLE 8-continued

Medium composition: YM medium (Difco) + 5% glucose + 1% soybean oil
4 mg/L ergosterol + 0–20 mg/L SQAD

| | | | Supernatant fraction | | | Cell fraction | | |
|---|---|---|---|---|---|---|---|---|
| | | | ($\mu$g/L of culture solution) | | | | | |
| Strain No. | SQAD | Days | NE | FOH | GGOH | NE | FOH | GGOH |
| | 1 | | 0.0 | 569.8 | 235.7 | 0.0 | 53.4 | 28.2 |
| | 20 | | 34.2 | 5513.3 | 360.4 | 0.0 | 537.5 | 84.5 |
| IFO 0974 | 0 | 3 | 0.0 | 24.8 | 11.1 | 0.0 | 3.3 | 0.0 |
| Kuraishia | 1 | | 0.0 | 1061.9 | 46.1 | 0.0 | 16.1 | 7.5 |
| capsulata | 20 | | 0.0 | 2022.7 | 262.0 | 0.0 | 149.2 | 34.8 |
| | 0 | 7 | 0.0 | 167.5 | 236.3 | 0.0 | 3.2 | 8.5 |
| | 1 | | 0.0 | 713.7 | 275.7 | 0.0 | 24.8 | 21.2 |
| | 20 | | 35.9 | 8268.5 | 680.4 | 0.0 | 362.1 | 59.7 |
| IFO 1472 | 0 | 3 | 0.0 | 34.8 | 79.8 | 0.0 | 7.4 | 20.4 |
| Ogataea | 1 | | 0.0 | 40.5 | 86.0 | 0.0 | 3.7 | 9.5 |
| glucozyma | 20 | | 0.0 | 808.8 | 278.7 | 0.0 | 41.1 | 37.5 |
| | 0 | 7 | 0.0 | 63.2 | 138.8 | 0.0 | 0.0 | 0.0 |
| | 1 | | 0.0 | 93.8 | 114.7 | 0.0 | 0.0 | 0.0 |
| | 20 | | 0.0 | 1832.0 | 513.0 | 0.0 | 73.7 | 52.6 |
| IFO 1892 | 0 | 3 | 0.0 | 70.4 | 46.1 | 0.0 | 3.7 | 0.0 |
| Saccharomyces | 1 | | 0.0 | 51.4 | 23.0 | 0.0 | 2.3 | 0.0 |
| kluyeri | 20 | | 0.0 | 62.9 | 30.7 | 0.0 | 16.5 | 0.0 |
| | 0 | 7 | 0.0 | 158.5 | 71.4 | 0.0 | 0.0 | 0.0 |
| | 1 | | 23.5 | 188.3 | 101.7 | 0.0 | 5.0 | 0.0 |
| | 20 | | 44.1 | 935.3 | 126.4 | 0.0 | 227.8 | 27.8 |
| IFO 1910 | 0 | 3 | 0.0 | 11.0 | 44.7 | 0.0 | 0.0 | 0.0 |
| Candida | 1 | | 0.0 | 20.9 | 69.3 | 0.0 | 0.0 | 0.0 |
| cariosilignicola | 20 | | 0.0 | 124.9 | 127.1 | 0.0 | 8.1 | 19.6 |
| | 0 | 7 | 0.0 | 51.7 | 152.9 | 0.0 | 0.0 | 0.0 |
| | 1 | | 0.0 | 257.7 | 367.3 | 0.0 | 10.3 | 37.4 |
| | 20 | | 0.0 | 14378.1 | 2997.2 | 0.0 | 845.5 | 205.0 |
| IFO 0005 | 0 | 3 | 22.9 | 552.1 | 496.1 | 0.0 | 50.5 | 75.2 |
| Candia | 1 | | 260.0 | 6784.9 | 818.5 | 8.6 | 462.0 | 86.5 |
| glabrata | 20 | | 2384.0 | 37513.9 | 1022.9 | 423.9 | 9405.0 | 306.5 |
| | 0 | 7 | 77.1 | 1676.1 | 1434.6 | 0.0 | 41.2 | 51.2 |
| | 1 | | 546.0 | 11219.5 | 1377.8 | 9.2 | 331.7 | 77.1 |
| | 20 | | 6208.9 | 68495.6 | 3228.1 | 139.2 | 2682.5 | 217.6 |

NE: nerolidol
FOH: farnesol
GGOH: geranylgeraniol
SQAD: squalene synthesis inhibitor 0; none 1; 1 mg/L 20; 20 mg/L

Example 9

Combined Effects of Sugars and Fats or Oils on Prenyl Alcohol Secretory Production Each of the strains shown in Tables 9 and 10 below was cultured in YM, KB or KY medium supplemented with 1% soybean oil, 6% glucose, 4 mg/L ergosterol and 0 mg/L or 20 mg/L squalene synthesis inhibitor (SQAD) to examine the respective production of nerolidol, geranylgeraniol and farnesol in the same manner as stated above. The results are shown in Table 9 (supernatant fraction) and Table 10 (cell fraction).

As a control, each strain was cultured in YM medium without the above supplemental ingredients to examine the respective production of nerolidol, geranylgeraniol and farnesol in the same manner as stated above. Table 11 shows the results obtained.

These tables indicate that the addition of soybean oil, glucose and a squalene synthesis inhibitor effects an increased production in both the cell fraction and the supernatant fraction (i.e., an increased secretion from the cells).

TABLE 9

Medium composition: YM or KB or KY medium + 1% soybean oil + 6% glucose + 4 mg/L ergosterol

| | | | Supernatant fraction ($\mu$g/L) | | |
|---|---|---|---|---|---|
| Medium | Strain No. | SQAD | NE | FOH | GGOH |
| YM | IFO 0107 | 0 | 0.0 | 10.8 | 155.2 |
| | Saccharomycopsis fibuligera | 20 | 0.0 | 9.7 | 386.5 |
| KB | K 0876 | 0 | 0.0 | 29.0 | 0.0 |
| | Psendomonas sp: | 20 | 0.0 | 7.8 | 0.0 |
| YM | IFO 1665 | 0 | 0.0 | 4.7 | 211.5 |
| | Saccharomycopsis fibuligera | 20 | 0.0 | 94.5 | 4214.9 |
| YM | IFO 1744 | 0 | 0.0 | 0.0 | 155.5 |
| | Saccharomycopsis fibuligera | 20 | 0.0 | 41.1 | 3870.1 |
| KB | K 2103 | 0 | 0.0 | 10.9 | 0.0 |
| | Norcadia asteroides | 20 | 0.0 | 0.0 | 0.0 |
| KY | K 3009 | 0 | 0.0 | 0.0 | 36.5 |
| | Mucor Javanicus | 20 | 0.0 | 38.8 | 343.6 |
| KY | K 4003 | 0 | 30.1 | 511.9 | 694.7 |
| | Saccharomyces Hafe logos van Laer | 20 | 4980.0 | 56541.1 | 3603.4 |
| KY | K 4045 | 0 | 148.1 | 870.4 | 766.8 |
| | Saccharomyces cerevisiae | 20 | 24606.3 | 37772.7 | 2590.6 |

TABLE 9-continued

Medium composition: YM or KB or KY medium + 1% soybean oil + 6% glucose + 4 mg/L ergosterol

| | | | Supernatant fraction (μg/L) | | |
|---|---|---|---|---|---|
| Medium | Strain No. | SQAD | NE | FOH | GGOH |
| KY | K 4102 | 0 | 17.5 | 541.1 | 711.3 |
| | *Saccharomyces ellipsoideus* | 20 | 18160.8 | 50245.8 | 3207.1 |
| KY | K 4103 | 0 | 56.4 | 753.1 | 1072.8 |
| | *Saccharomyces cerevisiae* | 20 | 20930.8 | 53814.6 | 4589.9 |
| KY | K 4104 | 0 | 19.5 | 569.2 | 546.0 |
| | *Saccharomyces cerevisiae* | 20 | 23620.7 | 54713.2 | 2654.4 |
| KY | IFO 0565 | 0 | 0.0 | 411.7 | 535.2 |
| | *Saccharomyces cerevisiae* | 20 | 839.9 | 45723.6 | 2216.6 |
| KY | IFO 0210 | 0 | 37.5 | 685.5 | 362.8 |
| | *Saccharomyces cerevisiae* | 20 | 25251.0 | 48795.6 | 1627.2 |
| KY | IFO 0346 | 0 | 0.0 | 196.2 | 278.9 |
| | *Schizosaccharomyces pombe* | 20 | 757.6 | 45282.1 | 1153.6 |
| KY | IFO 1475 | 0 | 0.0 | 236.9 | 462.7 |
| | *Ogataea polymorpha* | 20 | 0.0 | 5643.0 | 1195.1 |
| KY | JCM 2169 | 0 | 0.0 | 809.8 | 241.2 |
| | *Debaryomyces vanrijiae var vanrijiae* | 20 | 129.5 | 20359.5 | 2236.0 |
| KY | IFO 0339 | 0 | 0.0 | 164.4 | 364.3 |
| | *Saccharomycodes ludwigii* | 20 | 131.0 | 28498.6 | 1483.8 |
| KY | IFO 0115 | 0 | 0.0 | 254.9 | 493.6 |
| | *Hanseniaspora valbyensis valbyensis* | 20 | 182.6 | 26807.1 | 1217.7 |
| KY | IFO 0648 | 0 | 0.0 | 136.4 | 433.8 |
| | *Kluyveromyces lactis* | 20 | 348.6 | 31785.7 | 3343.8 |
| KY | IFO 0005 | 0 | 192.8 | 861.5 | 909.0 |
| | *Candida glabrata* | 20 | 15504.1 | 44573.8 | 2237.1 |
| KY | IFO 0762 | 0 | 37.0 | 274.7 | 384.4 |
| | *Candida solani* | 20 | 1702.8 | 6574.7 | 619.1 |
| KY | IFO 1527 | 0 | 0.0 | 16.6 | 24.7 |
| | *Cryptococcus humicolus* | 20 | 0.0 | 49.6 | 33.4 |
| KY | IFO 1116 | 0 | 0.0 | 199.3 | 315.7 |
| | *Wickerhamia fluorescens* | 20 | 73.2 | 12200.1 | 1181.6 |

NE: nerolidol
FOH: farnesol
GGOH: geranylgeraniol
SQAD: squalene synthesis inhibitor 0; none 20; 20 mg/L
Treated with phosphatase

TABLE 10

Medium composition: YM or KB or KY medium + 1% soybean oil + 6% glucose + 4 mg/L ergosterol

| | | Cell fraction (μg/L) | | |
|---|---|---|---|---|
| Strain No. | SQAD | NE | FOH | GGOH |
| IFO 0107 | 0 | 0.0 | 8.1 | 24.6 |
| *Saccharomycopsis fibuligera* | 20 | 0.0 | 4.8 | 79.9 |
| K 0876 | 0 | 0.0 | 0.0 | 0.0 |
| *Psendomonas sp.* | 20 | 0.0 | 0.0 | 0.0 |
| IFO 1665 | 0 | 0.0 | 8.2 | 21.7 |
| *Saccharomycopsis fibuligera* | 20 | 0.0 | 20.8 | 228.9 |
| IFO 1744 | 0 | 0.0 | 0.0 | 42.2 |
| *Saccharomycopsis fibuligera* | 20 | 0.0 | 29.8 | 819.1 |
| K 2103 | 0 | | | |
| *Norcadia asteroides* | 20 | | | |
| K 3009 | 0 | 13.4 | 22.7 | 17.5 |
| *Mucor Javanicus* | 20 | 0.0 | 15.6 | 61.7 |
| K 4003 | 0 | 0.0 | 36.9 | 52.4 |
| *Saccharomyces Hafe logos van Laer* | 20 | 291.8 | 7433.0 | 710.6 |

TABLE 10-continued

Medium composition: YM or KB or KY medium + 1% soybean oil + 6% glucose + 4 mg/L ergosterol

| | | Cell fraction (μg/L) | | |
|---|---|---|---|---|
| Strain No. | SQAD | NE | FOH | GGOH |
| K 4045 | 0 | 0.0 | 69.3 | 65.8 |
| *Saccharomyces cerevisiae* | 20 | 3022.6 | 7893.0 | 534.5 |
| K 4102 | 0 | 0.0 | 36.4 | 76.3 |
| *Saccharomyces ellipsoideus* | 20 | 1350.0 | 6358.2 | 396.5 |
| K 4103 | 0 | 0.0 | 591.7 | 39.4 |
| *Saccharomyces cerevisiae* | 20 | 1073.6 | 5528.9 | 369.6 |
| K 4104 | 0 | 0.0 | 51.6 | 79.2 |
| *Saccharomyces cerevisiae* | 20 | 2409.9 | 11464.9 | 656.2 |
| IFO 0565 | 0 | 0.0 | 40.2 | 54.7 |
| *Saccharomyces cerevisiae* | 20 | 57.3 | 5071.6 | 333.5 |
| IFO 0210 | 0 | 0.0 | 119.4 | 89.6 |
| *Saccharomyces cerevisiae* | 20 | 1698.7 | 4355.2 | 183.2 |
| IFO 0346 | 0 | 0.0 | 29.7 | 82.6 |
| *Schizosaccharomyces pombe* | 20 | 83.1 | 4826.5 | 159.4 |
| IFO 1475 | 0 | 0.0 | 31.4 | 126.0 |
| *Ogataea polymorpha* | 20 | 19.8 | 1196.1 | 402.7 |
| JCM 2169 | 0 | 0.0 | 67.2 | 54.3 |
| *Debaryomyces vanrijiae var vanrijiae* | 20 | 23.9 | 2807.0 | 492.6 |
| IFO 0339 | 0 | 0.0 | 41.6 | 114.7 |
| *Saccharomycodes ludwigii* | 20 | 0.0 | 3217.2 | 199.4 |
| IFO 0115 | 0 | 0.0 | 25.2 | 76.6 |
| *Hanseniaspora valbyensis valbyensis* | 20 | 15.1 | 2823.5 | 185.8 |
| IFO 0648 | 0 | 0.0 | 20.9 | 84.6 |
| *Kluyveromyces lactis* | 20 | 14.5 | 1128.6 | 225.8 |
| IFO 0005 | 0 | 0.0 | 34.9 | 51.7 |
| *Candida glabrata* | 20 | 1193.0 | 4710.9 | 279.6 |
| IFO 0762 | 0 | 16.2 | 90.5 | 126.0 |
| *Candida solani* | 20 | 231.3 | 962.5 | 350.0 |
| IFO 1527 | 0 | 7.8 | 16.0 | 0.0 |
| *Cryptococcus humicolus* | 20 | 21.2 | 160.9 | 51.9 |
| IFO 1116 | 0 | 0.0 | 15.0 | 86.5 |
| *Wickerhamia fluorescens* | 20 | 32.6 | 4262.8 | 500.7 |

NE: nerolidol
FOH: farnesol
GGOH: geranylgeraniol
SQAD: squalene synthesis inhibitor 0; none 20; 20 mg/L
Treated with phosphatase

TABLE 11

Medium composition: YM medium (Difco)

| | Supernatant fraction | | | Cell fraction | | |
|---|---|---|---|---|---|---|
| | (μg/L of culture solution) | | | | | |
| Strain No. | NE | FOH | GGOH | NE | FOH | GGOH |
| KB K 0876 | 0 | 18.6 | 0 | 0 | 0 | 0 |
| *Psendomonas sp.* | | | | | | |
| KB K 2103 | 14.2 | 0 | 0 | 0 | 0 | 0 |
| *Norcadia asteroides* | | | | | | |
| KY K 3009 | 0 | 0 | 0 | 0 | 0 | 0 |
| *Mucor Javanicus* | | | | | | |
| KY K 4003 | 0 | 5.0 | 0 | 0 | 19.3 | 0 |
| *Saccharomyces Hafe logos van Laer* | | | | | | |
| KY K 4045 | 0 | 0 | 0 | 0 | 44.9 | 18.6 |
| *Saccharomyces cerevisiae* | | | | | | |
| KY K 4102 | 0 | 0 | 0 | 0 | 22.9 | 7.2 |
| *Saccharomyces ellipsoideus* | | | | | | |
| KY K 4103 | 0 | 0 | 0 | 0 | 22.6 | 8.6 |
| *Saccharomyces cerevisiae* | | | | | | |

TABLE 11-continued

Medium composition: YM medium (Difco)

| | Supernatant fraction | | | Cell fraction | | |
|---|---|---|---|---|---|---|
| | (μg/L of culture solution) | | | | | |
| Strain No. | NE | FOH | GGOH | NE | FOH | GGOH |
| KY K 4104 | 0 | 0 | 0 | 0 | 15.8 | 31.7 |
| Saccharomyces cerevisiae | | | | | | |
| KY IFO 0565 | 0 | 0 | 0 | 0 | 0 | 54.7 |
| Saccharomyces cerevisiae | | | | | | |
| KY IFO 0210 | 0 | 0 | 0 | 0 | 0 | 0 |
| Saccharomyces cerevisiae | | | | | | |
| KY IFO 0346 | 0 | 4.4 | 0 | 0 | 16.8 | 0 |
| Schizosaccharomyces pombe | | | | | | |
| KY IFO 1475 | 0 | 0 | 0 | 0 | 13.5 | 36.1 |
| Ogataea polymorpha | | | | | | |
| KY JCM 2169 | 0 | 73.7 | 0 | 0 | 14.3 | 6.2 |
| Debaryomyces vanrijiae var vanrijiae | | | | | | |
| KY IFO 0339 | 0 | 15.3 | 0 | 0 | 6.0 | 80.9 |
| Saccharomycodes ludwigii | | | | | | |
| KY IFO 0115 | 0 | 13.6 | 0 | 0 | 7.4 | 103.5 |
| Hanseniaspora valbyensis valbyensis | | | | | | |
| KY IFO 0648 | 0 | 6.0 | 0 | 0 | 6.3 | 72.9 |
| Kluyveromyces lactis | | | | | | |
| KY IFO 0005 | 0 | 35.7 | 5.4 | 0 | 4.5 | 28.3 |
| Candida glabrata | | | | | | |
| KY IFO 0762 | 0 | 0 | 0 | 0 | 0 | 29.0 |
| Candida solani | | | | | | |
| KY IFO 1527 | 0 | 0 | 0 | 0 | 0 | 0 |
| Cryptococcus humicolus | | | | | | |
| KY IFO 1116 | 0 | 18.7 | 0 | 0 | 4.2 | 23.0 |
| Wickerhamia fluorescens | | | | | | |

NE: nerolidol
FOH: farnesol
GGOH: geranylgeraniol
Treated with phosphatase

Example 10

Combined Effects of Surfactants, Sugars and Fats or Oils on Prenyl Alcohol Secretory Production Each of the strains shown in Table 12 below was cultured in Medium A (YM medium supplemented with 0.1% Adekanol and 4 mg/L ergosterol) or Medium B (YM medium supplemented with 0.1% Adekanol, 4 mg/L ergosterol, 5% glucose and 3% soybean oil) at 30° C. for 4 or 10 days to examine the respective production of nerolidol, geranylgeraniol and farnesol in the same manner as stated above. Table 12 also shows the results obtained (supernatant and cell fractions).

TABLE 12

Medium composition:
Medium A: YM medium + 0.1% Adekanol + 4 mg/L ergosterol
Medium B: YM medium + 0.1% Adekanol + 4 mg/L ergosterol + 5% glucose + 3% soybean oil

| | Culti-vation | Medium A | | | Medium B | | |
|---|---|---|---|---|---|---|---|
| | | (μg/L of culture solution) | | | | | |
| Strain No. | days | NE | FOH | GGOH | NE | FOH | GGOH |
| ATCC 20864 | 4 | 0.0 | 0.0 | 0.0 | 0.0 | 62.8 | 64.7 |
| Pichia pastorias | 10 | 0.0 | 0.0 | 0.0 | 0.0 | 0.0 | 134.1 |
| IFO 0638 | 4 | 0.0 | 0.0 | 0.0 | 0.0 | 66.4 | 16.7 |
| Schizosaccharomyces pombe | 10 | 0.0 | 0.0 | 0.0 | 0.0 | 52.8 | 22.1 |
| ATCC 76625 | 4 | 0.0 | 0.0 | 0.0 | 0.0 | 34.2 | 0.0 |
| Saccharomyces cerevisiae | 10 | 0.0 | 0.0 | 0.0 | 0.0 | 48.9 | 27.8 |

FOH: farnesol
GGOH: geranylgeraniol
NE: nerolidol

Example 11

Combined Effects of Sugars and Fats or Oils on Prenyl Alcohol Secretory Production Each bacterial strain detected to produce farnesol was cultured in KB medium supplemented with 1% soybean oil, 4 mg/L ergosterol, and 0 mg/L or 20 mg/L squalene synthesis inhibitor (SQAD) to examine the respective production of nerolidol, geranylgeraniol and farnesol in the same manner as stated above. Table 13 shows the results obtained.

As a control, each strain was cultured in KB medium without the above supplemental ingredients to examine the respective production of nerolidol, geranylgeraniol and farnesol in the same manner as stated above. Table 14 shows the results obtained.

These tables indicate that the addition of a squalene synthesis inhibitor effects an increased production in bacterial strains as in the case of yeast strains.

TABLE 13

Medium composition: KB medium + 1% soybean oil + ergosterol

| | | Supernatant fraction | | | Cell fraction | | |
|---|---|---|---|---|---|---|---|
| | | (μg/L of culture solution) | | | | | |
| Strain No. | SQAD | NE | FOH | GGOH | NE | FOH | GGOH |
| IFO 3032 | 0 | 0.0 | 11.6 | 0.0 | 0.0 | 0.0 | 0.0 |
| Baccilus amyloliquefaciens | 20 | 0.0 | 22.4 | 0.0 | 0.0 | 0.0 | 0.0 |
| IFO 3030 | 0 | 0.0 | 21.9 | 0.0 | 0.0 | 0.0 | 0.0 |
| Baccilus pumilus | 20 | 0.0 | 36.6 | 0.0 | 0.0 | 6.0 | 0.0 |
| IFO 3762 | 0 | 0.0 | 6.8 | 0.0 | 0.0 | 11.2 | 0.0 |
| Staphylococcus epidermidis | 20 | 0.0 | 121.4 | 0.0 | 0.0 | 292.4 | 0.0 |
| IFO 3067 | 0 | 0.0 | 5.1 | 0.0 | 0.0 | 0.0 | 0.0 |
| Micrococcus lutenus | 20 | 0.0 | 57.3 | 0.0 | 0.0 | 11.8 | 0.0 |
| IFO 12146 | 0 | 0.0 | 0.0 | 0.0 | 0.0 | 0.0 | 0.0 |
| Exiguobacterium acetylicum | 20 | 0.0 | 115.7 | 0.0 | 0.0 | 10.4 | 0.0 |

NE: nerolidol
FOH: farnesol
GGOH: geranylgeraniol
SQAD: squalene synthesis inhibitor 0; none 20; 20 mg/L
Treated with phosphatase

TABLE 14

Medium composition: KB medium

| | Supernatant fraction | | | Cell fraction | | |
|---|---|---|---|---|---|---|
| | (μg/L of culture solution) | | | | | |
| Strain No. | NE | FOH | GGOH | NE | FOH | GGOH |
| IFO 3032 *Baccilus amyloliquefaciens* | 0.0 | 4.1 | 0.0 | 0.0 | 0.0 | 0.0 |
| IFO 3030 *Baccilus pumilus* | 0.0 | 6.0 | 0.0 | 0.0 | 0.0 | 0.0 |
| IFO 3762 *Staphylococcus epidermidis* | 0.0 | 6.1 | 0.0 | 0.0 | 0.0 | 0.0 |
| IFO 3067 *Micrococcus lutenus* | 0.0 | 0.0 | 0.0 | 0.0 | 0.0 | 0.0 |

NE: nerolidol
FOH: farnesol
GGOH: geranylgeraniol
Treated with phosphatase

Example 12

Mass Production of Geranylgeraniol Using Recombinant Yeast

*Saccharomyces cerevisiae* strain pRS435GGF/pRS434GAP-HMG1/YPH499#1 was prepared and cultured in a 5 L jar fermenter in the following manner. This strain allows high level expression of the HMG CoA reductase gene and a fusion gene comprising the geranylgeranyl pyrophosphate synthase gene and the farnesyl pyrophosphate synthase gene.

(1) Obtaining of GGPS and HMG-CoAR1 Genes Derived from Yeast *Saccharomyces cerevisiae*

Based on the GenBank information of *S. cerevisiae*-derived GGPS (A.N.U 31632) and HMG-CoAR1 (A.N.M 22002) genes, the following primers matching N- and C-termini of these genes were prepared and then used for PCR along with a yeast cDNA library (TOYOBO No. CL7220-1) as a template under the following conditions. PCR of the HMG-CoAR1 gene was performed using Perfect match (Stratagene).

Primers

For GGPS:
N-terminal
5'-atg gag gcc aag ata gat gag ct-3'  (SEQ ID NO:1)

C-terminal
5'-tca caa ttc gga taa gtg gtc ta-3'  (SEQ ID NO:2)

For HMG-CoAR1:
N-terminal
5'-atg ccg ccg cta ttc aag gga ct-3'  (SEQ ID NO:3)

C-terminal
5'-tta gga ttt aat gca ggt gac gg-3'  (SEQ ID NO:4)

PCR conditions

Denaturation    94° C. for 45 seconds
Annealing       55° C. for 1 minute
Extension       72° C. for 2 minutes PCR fragments were confirmed at positions of interest (about 1.0 kbp and 3.2 kbp, respectively). These gene fragments were then cloned into a TA-clonable pT7Blue-T vector to determine the full nucleotide sequence of GGPS and about 40% nucleotide sequence of HMG-CoAR1. The resulting sequences were completely matched with the GenBank sequences and therefore confirmed as genes derived from *S. cerevisiae*.

The resulting vector carrying the HMG-CoAR1 gene cloned into the pT7Blue-T vector was designated pT7HMG1.

(2) Construction of Vector pYES2 for Expression in Yeast Cells (Preparation of pYES-GGPS6)

pYES2 (Invitrogen) is a shuttle vector for extraction in yeast cells, which carries yeast 2 μm DNA ori as a replication origin and GAL1 promoter inducible with galactose. pT7Blue-T vector carrying the cloned GGPS gene was treated with BamHI and SalI to collect the GGPS gene, which was then introduced into a BamHI-XhoI site of pYES2 to give a vector designated pYES-GGPS6.

(3) Cloning of Farnesyl Pyrophosphate Synthase Gene (FPS) ERG20 Derived from Yeast *Saccharomyces cerevisiae*

Using the following primers, the FPP synthase gene, ERG20, was cloned from *Saccharomyces cerevisiae* YPH499 (Stratagene) cDNA by PCR:

Primer 1 (SCFPS1):
5'-ATG GCT TCA GAA AAA GAA ATT AG-3'  (SEQ ID NO:5)

Primer 2 (SCFPS2):
5'-CTA TTT GCT TCT CTT GTA AAC TT-3'  (SEQ ID NO:6)

An amplified fragment of approximately 0.9 kbp was purified by agarose gel electrophoresis and then T/A ligated into pT7Blue-T to prepare plasmid DNA designated pT7ERG20.

(4) Construction of Expression Vector (4-1) Preparation of pRS405Tcyc and pRS404Tcyc (insertion of CYC1t fragments into pRS vectors)

CYC1 transcription terminator CYC1t fragments were prepared by PCR using the following primer sets.

Primers (i) CYC1t-XK
XhoI-Tcyc1FW:  5'-TGC ATC TCG AGG GCC GCA TCA TGT AAT TAG-3  (SEQ ID NO:7)

KpnI-Tcyc1RV:  5'-CAT TAG GTA CCG CCG CAA TAA AGC CTT CG-3'  (SEQ ID NO:8)

(ii) CYC1tXA
XhoI-Tcyc1FW:  5'-TGC ATC TCG AGG GCC GCA TCA TGT AAT TAG-3'  (SEQ ID NO:9)

ApaI-Tcyc1RV:  5'-CAT TAG GGC CCG CCG CAA TAA AGC CTT CG-3'  (SEQ ID NO:10)

```
                              -continued
PCR conditions

Template:      pYES2 (Invitrogen) 0.1 µg
Primer:        50 pmol primer DNA
PCR solution:  50 µl reaction cocktail containing:
               1 x pfu buffer with MgSO4 (Promega, Madison, WI),
               10 nmol dNTP,
               1.5 u Pfu DNA polymerase (Promega), and
               1 µl perfect match polymerase enhancer (Stratagene)
Reaction:      95° C. for 2 minutes, (95° C. for 45 seconds, 60° C. for
               30 seconds, 72° C. for 1 minute) x 30 cycles, 72° C. for
               5 minutes, stored at 4° C.
```

The DNA fragments amplified with the above primer sets (i) and (ii) were cleaved with XhoI plus KpnI and XhoI plus ApaI, respectively, and then electrophoresed on agarose gels to give purified 260 bp DNA fragments designated CYC1t-XK and CYC1tXA. CYC1t-XK and CYC1tXA were inserted into a XhoI-KpnI site of pRS405 (Stratagene) and a XhoI-ApaI site of pRS404 (Stratagene), respectively, to give plasmids designated pRS405Tcyc and pRS404Tcyc.

(4-2) Preparation of TDH3p (Preparation of Transcription Promoter)

*Saccharomyces cerevisiae* YPH499 (Stratagene) genomic DNA was prepared using a yeast genomic DNA preparation kit "Gen TLE" (Takara Shuzo, Co., Ltd.), and then used as a PCR template to prepare a DNA fragment containing TDH3p (PGK) promoter.

(4-4) Preparation of pRS434GAP and pRS435GAP (Preparation of YEp-type Expression Vector)

$2\mu$OriSN was inserted into a NaeI site of pRS404Tcyc or pRS405Tcyc treated with BAP (bacterial alkaline phosphatase, TaKaRa), and then transformed into *E. coli* SURE2 to prepare plasmid DNA. The resulting plasmid DNA was cleaved with DraIII plus EcoRI, HpaI, or PstI plus PvuII, and then electrophoresed on an agarose gel to confirm the insertion and orientation of $2\mu$ori. pRS404Tcyc and pRS405Tcyc carrying $2\mu$ori inserted in the same orientation as pYES2 were designated pRS434Tcyc$2\mu$Ori and pRS435Tcyc$2\mu$Ori, respectively. The fragment TDH3p containing the transcription promoter was inserted into SacI-SacII sites of these two plasmids pRS434Tcyc$2\mu$Ori and pRS435Tcyc$2\mu$Ori to give plasmids designated pRS434GAP and pRS435GAP, respectively.

```
Primers

DNA primer      100 pmol
SacI-Ptdh3FW:   5'-CAC GGA GCT CCA GTT CGA GTT TAT CAT TAT CAA-3'    (SEQ ID NO:11)

SacII-Ptdh3RV:  5'-CTC TCC GCG GTT TGT TTG TTT ATG TGT GTT TAT TC-3' (SEQ ID NO:12)

PCR conditions

Template:      Saccharomyces cerevisiae YPH499 (Stratagene)
               genomic DNA 0.46 µg
PCR solution:  100 µl reaction cocktail containing:
               1 x ExTaq buffer (TaKaRa),
               20 nmol dNTP,
               0.5 u ExTaq DNA polymerase (TaKaRa), and
               1 µl perfect match polymerase enhancer
Reaction:      95° C. for 2 minutes, (95° C. for 45 seconds, 60° C. for 1 minute,
               72° C. for 2 minutes) x 30 cycles, 72° C. for 4 minutes, stored at
               4° C.
```

The amplified DNA fragment was cleaved with SacI and SacII, and then electrophoresed on an agarose gel to give a purified 680 bp DNA fragment designated TDH3p.

(4-3) Preparation of $2\mu$OriSN (Preparation of $2\mu$DNA Replication Origin Region)

pYES2 (Invitrogen) was cleaved with SspI and NheI, and then electrophoresed on an agarose gel to give a purified 1.5 kbp fragment containing the $2\mu$DNA replication origin ($2\mu$Ori). The resulting fragment was blunt-ended with Klenow enzyme and designated $2\mu$OriSN.

(5) Preparation of pRS435GGF (FPS-GGPS Fusion Protein Gene)

pYES-GGPS6 carrying the inserted GGPS gene BTS1 and pT7-ERG20 carrying the inserted FPS gene ERG20 were used as templates to perform PCR under the following conditions.

```
(i) PCR1

Template: pYES-GGPS6
Primer 1: SacII-BTS1, 5'-TCC CCG CGG ATG GAG GCC AAG ATA GAT-3'    (SEQ ID NO: 13)

Primer 2: BTSI-109I, 5'-GCA GGG ACC CCA ATT CGG ATA AGT GGT C-3'   (SEQ ID NO: 14)
``` wherein the sequence CCG CGG in primer 1 represents a SacII, XhoI or XbaI recognition site for vector ligation, and the sequence GGG ACC C in primer 2 represents a EcoO109I recognition site for fusion gene preparation.

(ii) PCR2

Template: pT7-ERG20
Primer 3: 109I-ERG20, 5'-GTA GGG TCC TCA GAA AAA GAA ATT AGG AG-3' (SEQ ID NO:15)

Primer 4: -21, 5'-TGT AAA ACG ACG GCC AGT-3'; (SEQ ID NO:16);

T7, 5'-TAA TAC GAC (SEQ ID NO:17)
TCA CTA TAG
GG-3' wherein the sequence GGG TCC T in primer 3 represents a EcoO109I recognition site for fusion gene preparation.

| PCR solution: | 50 µl reaction cocktail containing: |
| --- | --- |
| | 1 × KOD-Plus buffer (Toyobo, Osaka, Japan), |
| | 0.2 mM dNTPs, |
| | 0.25 mM MgSO$_4$, |
| | 15 pmol premer 1, |
| | 15 pmol primer 2, |
| | 0.01–0.1 µg template DNA, and |
| | 1u KOD-Plus DNA polymerase (Toyobo) |
| | (KOD-Plus contains 1.6 µg/µl KOD antibody) |
| Reaction: | 94° C. for 2 minutes, (94° C. for 15 seconds, |
| | 55° C. for 30 seconds, 68° C. for 1 |
| | minute) × 30 cycles, held at 68° C. for 2 minutes |

The reaction products obtained by (i) and (ii) above were designated #9 and #11, respectively. After cleavage with restriction enzyme EcoO109I, #9 and #11 were ligated to each other and then used as a PCR template to perform a second round of PCR using the above SacII-BTS1 and -21 as primers under the same conditions, thereby obtaining DNA fragment #9–#11. The second PCR product #9–#11 was cleaved with SacII and BamHI, and then inserted into a SacII-BamHI site of pRS435GAP to obtain pRS435GGF.

As expression vectors for non-fusion genes BTS1 and ERG20, pRS435GAP-BTS1, pRS445GAP-BTS1, pRS435GAP-ERG20 and pRS445GAP-ERG20 were used. pRS434TEF-HMG1 and pRS434GAP-HMG1 were used for HMG1 expression.

(6) Preparation of pRS434GAP-HMG1 pT7HMG1 was cleaved with SmaI and SalI and then electrophoresed on an agarose gel to give a purified 3.2 kbp HMG1 gene fragment. This fragment was inserted into a SmaI-SalI site of pRS434GAP to obtain pRS434GAP-HMG 1.

(7) Creation of Transgenic Yeast (pRS435GGF/pRS434GAP-HMG1/YPH499#1)

pRS435GGF and pRS434GAP-HMG1 were introduced into *Saccharomyces cerevisiae* strain YPH499 (Stratagene) using the lithium acetate method described in "Introduction of DNA into Yeast Cells" Current Protocols in Molecular Biology, John Wiley & Sons, Inc., pp. 13.7.1–13.7.2 (contributed by Daniel M. Becher and Victoria Lundblad) or a Frozen-EZ Yeast Transformation II technique (Zymo Research, Orange, Calif.). The transformant was cultured on SD (-URA) medium to select a colony growing at 30° C. on a SD (-URA) agar plate (DOB+CSM (-URA), BIO 101, Vista, Calif.), thereby obtaining pRS435GGF/pRS434GAP-HMG1/YPH499#1.

(8) Culture of Transgenic Yeast (pRS435GGF/pRS434GAP-HMG1/YPH499#1)

A loopful of the colony was inoculated from the slant into a 500 ml baffled Erlenmeyer flask containing 200 ml of SD-Leu-Trp medium (BIO 101 Inc.) supplemented with 40 mg/L adenine (Sigma). After culturing at 130 rpm and at 30° C. for 2 days, centrifugation (1500×g, 5 minutes, 4° C.) and washing with sterilized physiological saline were repeated three times to completely remove glucose contained in the culture solution. An aliquot of the culture solution (50 ml; 1%) was then inoculated into a fermenter.

Fermentation Medium

5% glucose (including 1% glucose originally contained in YM broth)

YM broth (Difco)

0% or 3% soybean oil (Nacalai)

0.1% Adekanol LG-109 (Asahi Denka Kogyo K.K.)

Operation Conditions

Culture apparatus: MSJ-U 10 L culture apparatus (B. E. Marubishi Co., Ltd.)

Medium volume: 5 L

Medium temperature: 33° C.

Aeration rate: 1 vvm

Agitation: 300 rpm pH: pH is proportionally controlled with 4N sodium hydroxide and 2N hydrochloric acid under the following parameter conditions, unless otherwise specified:

| Proportional Band | 1.00 |
| --- | --- |
| Non Sensitive Band | 0.15 |
| Control Period | 16 sec |
| Full Stroke | 1 sec |
| Minimum Stroke | 0 sec |

Figure 10:
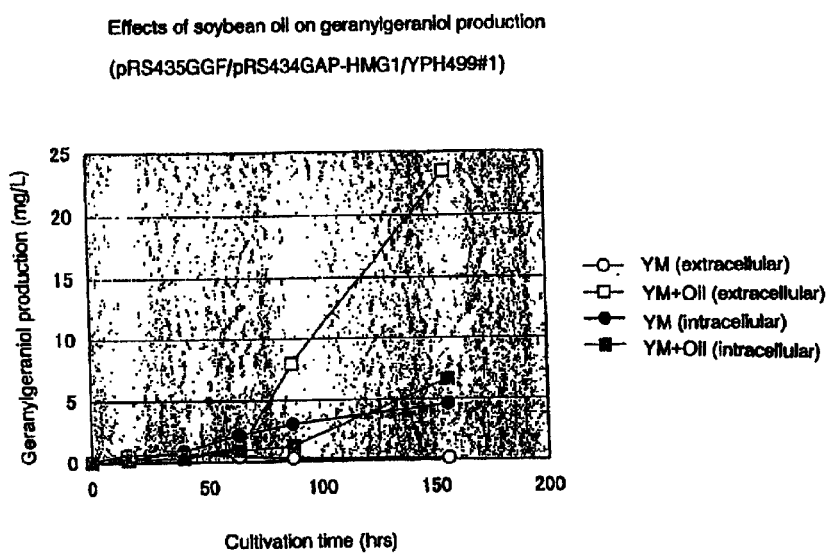
FIG. 10 shows effects of a fat or oil on geranylgeraniol secretory production in recombinant yeast cells.

Analyses of extracellular and intracellular geranylgeraniol indicate that the addition of soybean oil allows geranylgeraniol to be secreted from the cells. The addition of soybean oil also resulted in an approximately 4-fold increase in production per se (FIG. 10).

Example 13

Mass Production of Farnesol Using Recombinant Yeast

Farnesol-producing recombinant yeast strain pYHMG044/AURGG101 was prepared and cultured in the following manner.

(1) Preparation of HMG1Δ Expression Vector pYHMG044 pT7HMG1 prepared in Example 12 was used as a template to prepare a fragment containing the vector backbone and a partially deleted HMG1 coding region by PCR. The resulting fragment was blunt-ended with Klenow enzyme, re-cyclized through self-ligation, and then transformed into *E. coli* JM109 to prepare plasmid DNA pYHMG044. The synthetic DNA sequences used as a primer set are presented below.

Primers

```
                                            (SEQ ID NO:18)
5'-AGA AGA TAC GGA TTT CTT TTC TGC TTT-3'

(SEQ ID NO:19)
5'-AAC TTT GGT GCA AAT TGG GTC AAT GAT-3'
```

By using a 373A DNA sequencer (Perkin Elmer, Foster City, Calif.), the resulting DNA plasmid was confirmed to show no shift in reading frame for amino acids located upstream and downstream of HMG1 and to contain no PCR error-based amino acid replacement in the neighborhood of its binding site.

(2) Preparation of AURGG101 pAUR101 (TaKaRa, Japan) was linearized with EcoO65I and then introduced into *Saccharomyces cerevisiae* strain A451 (ATCC 200598) according to the lithium acetate method described in "Introduction of DNA into Yeast Cells" Current Protocols in Molecular Biology, John Wiley & Sons, Inc., pp. 13.7.1–13.7.2 (contributed by Daniel M. Becher and Victoria Lundblad). The transformant was cultured on an YPD agar plate (1% yeast extract, 2% peptone, 2% dextrose, 2% agar) containing 1 µg/ml Aureobasidin to select a colony growing thereon at 30° C.

(3) Creation of Transgenic Yeast (pYHMG044/AURGG 101)

pYHMG044 was introduced into AURGG101 according to the lithium acetate method described in "Introduction of DNA into Yeast Cells" Current Protocols in Molecular Biology, John Wiley & Sons, Inc., pp.13.7.1–13.7.2 (contributed by Daniel M. Becher and Victoria Lundblad). The transformant was cultured on SD (-URA) medium to select a colony growing at 30° C. on an SD (-URA) agar plate (DOB+CSM (-URA), BIO 101, Vista, Calif.), thereby obtaining pYHMG044/AURGG101.

(4) Culture Conditions

A loopful of the recombinant yeast strain pYHMG044/AURGG101 was inoculated from the slant into 200 ml of CSM-URA (BIO 101 Inc.) and DOB (BIO 101 Inc.) medium in a 500 ml baffled Erlenmeyer flask. After culturing at 130 rpm and at 30° C. for 2 days, centrifugation (1500×g, 5 minutes, 4° C.) and washing with sterilized physiological saline were repeated three times to completely remove glucose contained in the culture solution. An aliquot of the culture solution (50 ml; 1%) was then inoculated into a fermenter.

Fermentation Medium

5% glucose

YNB containing all amino acids (Difco)

1% soybean oil (Nacalai)

0.1% Adekanol LG-109 (Asahi Denka Kogyo K.K.)

Operation Conditions

Culture apparatus: MSJ-U 10 L culture apparatus (B. E. Marubishi Co., Ltd.)

Medium volume: 5 L

Medium temperature: 26° C.

Aeration rate: 1 vvm

Agitation: 300 rpm pH: pH is proportionally controlled with 4N sodium hydroxide and 2N hydrochloric acid under the following parameter conditions, unless otherwise specified:

| | |
|---|---|
| Proportional Band | 1.00 |
| Non Sensitive Band | 0.15 |
| Control Period | 16 sec |
| Full Stroke | 1 sec |
| Minimum Stroke | 0 sec |

Figure 11:
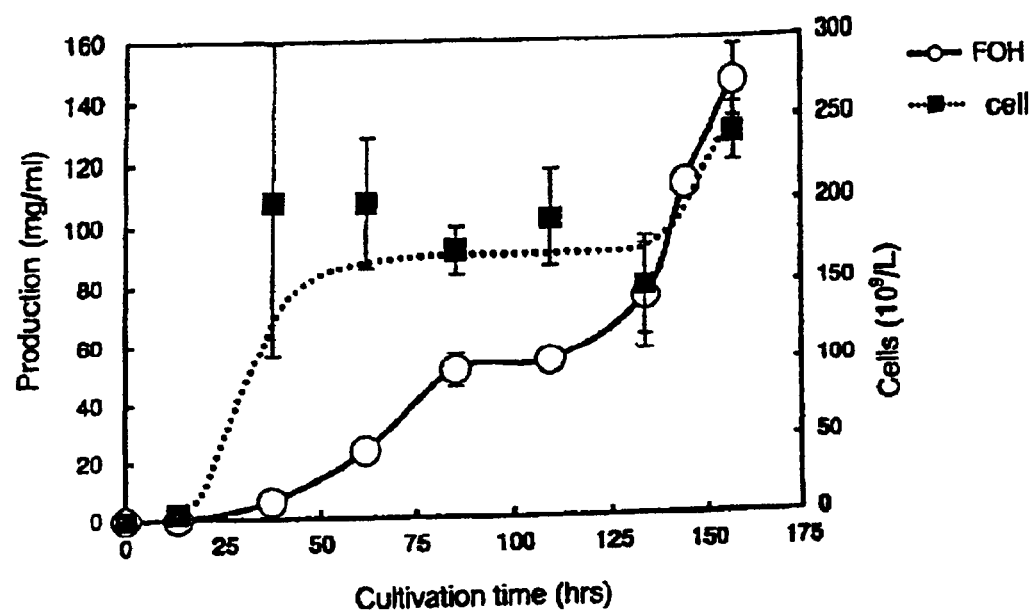
FIG. 11 shows effects of a fat or oil on farnesol secretory production in recombinant yeast cells.

Cell counting was performed on 100 µl culture solution diluted 1- to 20-fold with physiological saline using a hemocytometer (supplier: HAYASHI RIKAGAKU, manufacturer: Sunlead Glass Co.). Cells found in a 0.06 mm square (corresponding to 9 minimum grids) were averaged over quadruplicate measurements to calculate cell counts per liter of culture medium from the following equation:

Cell counts ($1 \times 10^9$/L broth)=0.444×(cell counts in 0.06 mm square)×dilution factor Soybean oil stimulated the secretory production of farnesol in recombinant yeast cells. It allowed farnesol to be secreted from the cells in an amount of approximately 150 mg/L over 150 hours (FIG. 11).

Example 14

Under the culture conditions shown in Table 15 (e.g., days of culture, culture temperature, type of medium), various strains were cultured according to the same culture procedures as described in Example 1, followed by extraction of prenyl alcohol from both cell and supernatant fractions. Analysis was performed on these fractions according to the procedures presented in the Reference Example. Table 15 also shows the results obtained. LBO-SSI, YPDO-SSI, YMO-SSI, YMOL-SSI and HVO-SSI media used in this example were prepared as follows.

LBO-SSI Medium

The following ingredients were dissolved in 1 L of deionized water and then autoclaved. After the autoclaved medium was fully cooled, a filter-sterilized aqueous solution of squalene synthase inhibitor SQAD (2.5 mg/ml) was added to the medium to give a final concentration of 20 mg/L.

| | |
|---|---|
| Yeast Extract (Difco) | 5 g |
| Bactopeptone (Difco) | 10 g |
| NaCl (Nacalai) | 5 g |
| Glucose (Nacalai) | 50 g |
| Soybean oil (Nacalai) | 10 ml |
| Ergosterol solution | 200 µl (200 µl of 20 mg/ml solution in 50% EtOH-50% Tergitol) |

YPDO-SSI Medium

The following ingredients were dissolved in 1 L of deionized water and then autoclaved. After the autoclaved medium was fully cooled, a filter-sterilized aqueous solution of squalene synthase inhibitor SQAD (2.5 mg/ml) was added to the medium to give a final concentration of 20 mg/L.

| | |
|---|---|
| Yeast Extract (Difco) | 10 g |
| Bactopeptone (Difco) | 20 g |
| Glucose (Nacalai) | 50 g |
| Soybean oil (Nacalai) | 10 ml |

-continued

| | |
|---|---|
| Ergosterol solution | 200 μl (200 μl of 20 mg/ml solution in 50% EtOH-50% Tergitol) |

YMO-SSI Medium

The following ingredients were added to YM medium (Difco), adjusted to 1 L with deionized water and then autoclaved. After the autoclaved medium was fully cooled, a filter-sterilized aqueous solution of squalene synthase inhibitor SQAD (2.5 mg/ml; Eisai Co., Ltd.) was added to the medium to give a final concentration of 1 to 20 mg/L.

| | |
|---|---|
| Glucose (Nacalai) | 50 g |
| Soybean oil (Nacalai) | 10 ml |
| Ergosterol (Nacalai) | 4 mg (200 μl of 20 mg/ml solution in 50% EtOH-50% Tergitol) |

YMOL-SSI Medium

This medium was prepared by adding 10 ml of olive oil (Nacalai) to YMO medium in the same manner as used for YMO-SSI preparation.

HVO-SSI Medium

The following ingredients were dissolved in 1 L of deionized water and then autoclaved. After the autoclaved medium was fully cooled, a filter-sterilized aqueous solution of squalene synthase inhibitor SQAD (2.5 mg/ml) was added to the medium to give a final concentration of 20 mg/L.

| | |
|---|---|
| NaCl (Nacalai) | 156 g |
| $MgCl_2.6H_2O$ (Nacalai) | 13 g |
| $MgSO_4.7H_2O$ (Nacalai) | 20 g |
| $CaCl_2.2H_2O$ (Nacalai) | 1 g |
| KCl (Nacalai) | 4 g |
| $NaHCO_3$ (Nacalai) | 0.2 g |
| KBr (Nacalai) | 0.5 g |
| Yeast Extract (Difco) | 5 g |
| Glucose (Nacalai) | 50 g |
| Soybean oil (Nacalai) | 10 ml |
| Ergosterol solution | 200 μl (200 μl of 20 mg/ml solution in 50% EtOH-50% Tergitol) |

TABLE 15

Production of nerolidol (NOH), farnesol (FOH) and geranylgeraniol (GGOH) (mg/L of culture solution)

| | | Day 3 | | | Day 10 | | | | |
|---|---|---|---|---|---|---|---|---|---|
| Strains | No. | NOH | FOH | GGOH | NOH | FOH | GGOH | Temp. | Medium |
| Alcaligenes faecalis | IFO 13111 | 0.00 | 0.01 | 0.11 | 0.00 | 0.04 | 0.09 | 30 | LBO-SSI |
| Brevibacterium divaricatum | NRRL 2311 | 0.00 | 0.00 | 0.02 | 0.00 | 0.00 | 0.00 | 30 | LBO-SSI |
| Brevibacterium fuscum | IFO 12127 | 0.00 | 0.02 | 0.00 | 0.00 | 0.00 | 0.00 | 30 | LBO-SSI |
| Brevibacterium linens | IFO 12171 | 0.00 | 0.46 | 0.00 | 0.00 | 0.08 | 0.00 | 30 | LBO-SSI |
| Candida catenulata | IFO 0720 | 0.04 | 8.10 | 0.34 | 0.04 | 8.61 | 0.47 | 30 | YMO-SSI |
| Candida fragicola | IFO 1574 | 0.03 | 4.91 | 0.76 | 0.04 | 8.95 | 1.31 | 30 | YMO-SSI |
| Candida krusei | IFO 0013 | 0.04 | 6.99 | 0.29 | 0.06 | 13.65 | 0.86 | 30 | YMO-SSI |
| Candida lambica | IFO 1146 | 0.02 | 4.53 | 0.49 | 0.04 | 0.59 | 1.24 | 30 | YMO-SSI |
| Candida maltosa | IFO 1977 | 0.00 | 6.74 | 0.19 | 0.08 | 9.03 | 0.58 | 30 | YMO-SSI |
| Candida mycoderma | IFO 0164 | 0.02 | 5.45 | 0.20 | 0.03 | 4.69 | 0.17 | 30 | YMO-SSI |
| Candida parapsilosis | IFO 0708 | 0.00 | 1.76 | 0.17 | 0.01 | 5.13 | 0.25 | 30 | YMO-SSI |
| Candida rugosa | IFO 0591 | 0.00 | 0.90 | 0.08 | 0.00 | 4.20 | 0.19 | 30 | YMO-SSI |
| Candida succiphila | IFO 1911 | 0.00 | 2.44 | 0.25 | 0.00 | 0.00 | 0.00 | 30 | YMO-SSI |
| Candida tropicalis | IFO 0006 | | | | 0.17 | 9.04 | 0.00 | 30 | YMO-SSI |
| Candida zeylanoides | IFO 0719 | 0.00 | 1.43 | 0.29 | 0.00 | 7.38 | 1.24 | 30 | YMO-SSI |
| Cryptococcus albidus | IFO 0881 | 0.00 | 0.15 | 0.03 | 0.02 | 2.41 | 0.45 | 30 | YMO-SSI |
| Cryptococcus glutinis | IFO 1125 | 0.04 | 6.64 | 1.48 | 0.35 | 3.70 | 3.29 | 24 | YMO-SSI |
| Dipodascus ovetensis | IFO 1201 | 0.00 | 4.23 | 0.14 | 0.04 | 8.68 | 0.95 | 30 | YMO-SSI |
| Haloferax volcanii | IFO 14742 | 2.12 | 39.11 | 1.04 | 4.14 | 57.73 | 2.49 | 30 | HVO-SSI |
| Hanseniaspora valbyensis | IFO 1758 | 0.00 | 0.33 | 0.04 | 0.04 | 2.40 | 0.12 | 30 | YMO-SSI |
| Issatchenkia orientalis | IFO 1279 | 0.00 | 2.22 | 0.15 | 0.03 | 7.68 | 0.52 | 30 | YMO-SSI |
| Kloeckera africana | IFO 0868 | 1.09 | 10.90 | 0.81 | 1.10 | 6.29 | 0.17 | 30 | YMO-SSI |
| Kloeckera apiculata | IFO 0151 | 0.00 | 0.05 | 0.02 | 1.04 | 10.73 | 0.86 | 30 | YMO-SSI |
| Kluyveromyces marxianus | IFO 0617 | 0.09 | 14.48 | 0.87 | 0.13 | 16.29 | 1.71 | 30 | YMO-SSI |
| Kuraishia capsulata | IFO 0974 | 0.00 | 0.91 | 0.17 | 0.00 | 3.25 | 0.42 | 30 | YMO-SSI |
| Mortierella ramanniana | ATCC 24786 | | | | 0.00 | 0.76 | 0.13 | 24 | YMO-SSI |
| Nakazawaea holstii | IFO 0980 | 0.01 | 1.06 | 0.18 | 0.02 | 5.85 | 0.38 | 30 | YMO-SSI |
| Pichia capsulata | IFO 0984 | 0.00 | 0.63 | 0.04 | 0.04 | 4.17 | 0.11 | 30 | YMO-SSI |
| Pichia henricii | IFO 1477 | 0.00 | 3.20 | 0.12 | 0.00 | 3.24 | 0.00 | 30 | YMO-SSI |
| Pichia holstii | IFO 0980 | 0.04 | 6.22 | 0.22 | 0.04 | 2.79 | 0.65 | 30 | YMO-SSI |
| Pichia naganishii | IFO 1670 | 0.00 | 2.14 | 0.22 | 0.02 | 9.28 | 0.96 | 30 | YMO-SSI |
| Pichia rhodanensis | IFO 1272 | 0.03 | 3.34 | 0.91 | 0.46 | 26.57 | 10.29 | 30 | YMO-SSI |
| Pichia saitoi | IAM 4945 | 0.34 | 10.78 | 0.51 | 0.28 | 24.31 | 1.38 | 30 | YMO-SSI |
| Rhodosporidium toruloides | IFO 8766 | 0.88 | 6.59 | 2.47 | 0.72 | 2.47 | 2.52 | 24 | YMO-SSI |
| Rhodotorula aurantinaca | IFO 0951 | 0.01 | 3.14 | 0.18 | 0.03 | 6.11 | 0.50 | 30 | YMO-SSI |
| Rhodotorula rubra | IFO 0870 | 0.03 | 1.62 | 1.02 | 0.16 | 2.32 | 1.61 | 30 | YMO-SSI |
| Saccharomycopsis fibuligera | IFO 0105 | 0.00 | 0.06 | 1.68 | 0.00 | 5.71 | 4.79 | 30 | YMO-SSI |
| Saccharomycopsis lipolytica | IFO 1209 | 0.05 | 9.48 | 0.16 | 0.21 | 16.46 | 0.83 | 30 | YMO-SSI |
| Schizosaccharomyces octosporus | IAM 4842 | 0.00 | 1.24 | 0.03 | 0.00 | 1.79 | 0.08 | 30 | YMO-SSI |

TABLE 15-continued

Production of nerolidol (NOH), farnesol (FOH) and geranylgeraniol (GGOH) (mg/L of culture solution)

| Staphylococcus aureus | IFO 3060 | 0.00 | 0.06 | 0.00 | 0.00 | 0.05 | 0.00 | 30 | YMO-SSI |
|---|---|---|---|---|---|---|---|---|---|
| Torulaspora delbrueckii | IFO 1626 | 0.04 | 2.33 | 0.15 | 0.06 | 5.50 | 0.36 | 30 | YMO-SSI |
| Trichosporon cutaneum | IFO 1198 | 0.00 | 10.23 | 0.69 | 0.00 | 0.14 | 0.09 | 30 | YMO-SSI |
| Tsukamurella paurometabolum | IFO12160 | 0.00 | 0.07 | 0.00 | 0.00 | 0.06 | 0.00 | 30 | YMO-SSI |
| Yamadazyma farinosa | IFO 0193 | 0.00 | 1.27 | 0.18 | 0.00 | 2.36 | 0.82 | 30 | YMO-SSI |
| Yerroiwa lipolytica | IFO 0746 | 0.06 | 9.66 | 0.15 | 0.16 | 13.41 | 0.36 | 24 | YMO-SSI |
| Zygosaccharomyces japonicus | IFO 0595 | 0.05 | 0.77 | 0.05 | 0.10 | 2.17 | 0.15 | 30 | YMO-SSI |

| | | Day 3 | | | Day 10 | | | Temp. | |
|---|---|---|---|---|---|---|---|---|---|
| Strains | IFO No. | NOH | FOH | GGOH | NOH | FOH | GGOH | (° C.) | Medium |
| Ambrosiozyma ambrosiae | 10835 | 0.0 | 0.1 | 1.5 | 0.0 | 0.0 | 0.7 | 24 | YPDO-SSI |
| Ambrosiozyma monospora | 10751 | 0.0 | 1.0 | 0.3 | 0.0 | 4.8 | 1.4 | 24 | YMO-SSI |
| Ambrosiozyma philentoma | 1847 | 0.0 | 0.9 | 0.2 | 0.0 | 16.8 | 0.8 | 24 | YMO-SSI |
| Ambrosiozyma platypodis | 10752 | 0.0 | 1.7 | 0.1 | 0.0 | 48.6 | 1.4 | 24 | YMO-SSI |
| Bensingtonia intermedia | 10178 | 0.0 | 1.5 | 0.7 | 0.0 | 2.9 | 5.2 | 24 | YMO-SSI |
| Botryozyma nematodophila | 10830 | 0.0 | 2.5 | 0.3 | 0.0 | 5.6 | 2.8 | 24 | YPDO-SSI |
| Brettanomyces anomalus | 0627 | 0.0 | 18.0 | 0.4 | 0.6 | 16.7 | 0.0 | 24 | YMO-SSI |
| Brettanomyces bruxellensis | 0797 | 0.0 | 4.7 | 0.5 | 0.0 | 8.2 | 0.0 | 24 | YMO-SSI |
| Brettanomyces custersianus | 10735 | 0.0 | 0.1 | 1.4 | 0.0 | 20.0 | 0.6 | 24 | YMO-SSI |
| Bullera crocea | 10113 | 0.0 | 7.4 | 0.5 | 0.0 | 16.1 | 0.5 | 17 | YMO-SSI |
| Bullera sinensis | 10756 | 0.1 | 0.3 | 1.0 | 0.1 | 1.7 | 2.3 | 24 | YMO-SSI |
| Citeromyces matritensis | 0651 | 0.1 | 2.0 | 0.4 | 0.0 | 0.7 | 0.0 | 24 | YMO-SSI |
| Clavispora lusitaniae | 10059 | 0.0 | 1.0 | 0.3 | 0.1 | 9.2 | 9.1 | 24 | YMO-SSI |
| Cystofilobasidium infirmominiatum | 1057 | 5.7 | 14.9 | 2.6 | 10.8 | 48.4 | 3.6 | 24 | YMO-SSI |
| Debaryomyces occidentalis | 1842 | 0.0 | 0.7 | 0.2 | 0.0 | 0.4 | 4.1 | 24 | YMO-SSI |
| Dekkera bruxellensis | 1590 | 0.0 | 3.7 | 0.2 | 0.0 | 15.7 | 0.0 | 24 | YMO-SSI |
| Dipodascus armillariae | 10804 | 0.0 | 4.2 | 0.1 | 0.0 | 3.3 | 0.2 | 24 | YMO-SSI |
| Dipodascus tetrasperma | 10810 | 0.0 | 1.7 | 0.8 | 0.0 | 9.8 | 2.5 | 24 | YMO-SSI |
| Eremascus albus | 10811 | 0.0 | 0.0 | 4.8 | 0.0 | 0.0 | 3.6 | 24 | YMO-SSI |
| Eremascus fertilis | 0691 | 0.0 | 0.0 | 0.0 | 0.0 | 0.4 | 0.0 | 24 | YMO-SSI |
| Eremothecium gossypii | 1355 | 0.0 | 0.8 | 0.0 | 0.0 | 4.4 | 0.9 | 24 | YMO-SSI |
| Erythrobasidium hasegawianum | 1058 | 0.0 | 0.5 | 1.0 | 0.0 | 0.0 | 6.8 | 24 | YMO-SSI |
| Hanseniaspora guilliermondii | 1411 | 0.0 | 1.4 | 0.1 | 0.0 | 1.3 | 0.0 | 24 | YMO-SSI |
| Hanseniaspora uvarum | 10833 | 0.1 | 15.3 | 2.9 | 0.4 | 11.1 | 0.8 | 24 | YPDO-SSI |
| Kloeckeraspora vineae | 1415 | 0.4 | 3.4 | 0.3 | 0.7 | 1.2 | 0.0 | 24 | YMO-SSI |
| Kockovaella imperatae | 10522 | 0.0 | 3.2 | 3.5 | 0.0 | 19.5 | 6.2 | 24 | YMO-SSI |
| Kodamaea ohmeri | 0202 | 0.0 | 7.7 | 1.6 | 0.1 | 13.7 | 4.7 | 24 | YMO-SSI |
| Kurtzmanomyces nectairei | 10118 | 0.0 | 0.1 | 0.1 | 0.0 | 0.0 | 0.0 | 24 | YMO-SSI |
| Leucosporidium scottii | 1924 | 0.2 | 32.8 | 1.3 | 0.7 | 5.2 | 0.0 | 24 | YMO-SSI |
| Lodderomyces elongisporus | 1676 | 0.1 | 14.8 | 2.0 | 0.1 | 15.7 | 0.0 | 24 | YMO-SSI |
| Malassezia furfur | 0656 | 0.0 | 4.3 | 0.1 | 0.0 | 6.9 | 0.1 | 30 | YMOO-SSI |
| Metschnikowia hawaiiensis | 10791 | 0.0 | 0.0 | 0.3 | 0.0 | 0.0 | 0.2 | 24 | YPDO-SSI |
| Metschnikowia krissii | 1677 | 0.0 | 1.3 | 0.1 | 0.0 | 21.0 | 0.0 | 24 | YMO-SSI |
| Metschnikowia lunata | 1605 | 0.0 | 5.1 | 1.0 | 0.3 | 31.9 | 5.9 | 24 | YMO-SSI |
| Metschnikowia pulcherrima | 0863 | 0.0 | 10.5 | 0.2 | 0.1 | 15.4 | 0.3 | 24 | YMO-SSI |
| Mrakia frigida | 1926 | 0.5 | 25.3 | 0.3 | 0.3 | 11.3 | 0.1 | 12 | YMO-SSI |
| Myxozyma lipomycoides | 10351 | 0.7 | 23.3 | 5.4 | 1.3 | 35 | 1.1 | 24 | YMO-SSI |
| Nadsonia commutata | 10029 | 0.0 | 0.1 | 0.0 | 0.0 | 0.3 | 0.0 | 17 | YMO-SSI |
| Pachysolen tannophilus | 1007 | 0.0 | 0.1 | 0.1 | 0.0 | 1.9 | 1.4 | 24 | YMO-SSI |
| Pichia burtonii | 10837 | 0.0 | 3.0 | 1.1 | 0.0 | 7.5 | 1.7 | 24 | YMO-SSI |
| Pichia misumaiensis | 10221 | 0.3 | 20.8 | 1.8 | 1.0 | 14.5 | 2.0 | 24 | YMO-SSI |
| Pichia ofunaensis | 10709 | 0.0 | 0.1 | 0.1 | 0.0 | 0.0 | 0.0 | 24 | YMO-SSI |
| Pichia pijperi | 1290 | 0.5 | 5.1 | 0.6 | 0.5 | 6.4 | 0.5 | 24 | YMO-SSI |
| Saccharomyces transvaalensis | 1625 | 0.1 | 0.0 | 0.0 | 0.0 | 0.0 | 0.0 | 30 | YMO-SSI |
| Saccharomycodes sinensis | 10111 | 0.1 | 0.4 | 0.0 | 0.6 | 0.8 | 0.1 | 30 | YMO-SSI |
| Saccharomycopsis fibuligera | 10829 | 0.0 | 0.0 | 4.1 | 0.0 | 0.0 | 2.8 | 24 | YPDO-SSI |
| Saccharomycopsis javaensis | 1848 | 0.0 | 0.0 | 0.0 | 0.0 | 0.0 | 0.6 | 24 | YMO-SSI |
| Saccharomycopsis schoenii | 10683 | 0.1 | 5.3 | 0.4 | 0.5 | 28.3 | 2.3 | 24 | YMO-SSI |
| Saccharomycopsis synnaedendra | 1604 | 0.0 | 2.8 | 1.3 | 0.0 | 1.2 | 0.0 | 24 | YMO-SSI |
| Saccharomycopsis vini | 1748 | 0.0 | 3.9 | 0.4 | 0.0 | 23.2 | 6.4 | 24 | YMO-SSI |
| Saturnispora zaruensis | 1384 | 0.0 | 0.2 | 0.1 | 0.0 | 3.0 | 1.3 | 24 | YMO-SSI |
| Schizoblastosporion kobayasii | 1644 | 0.0 | 4.0 | 0.9 | 0.0 | 2.8 | 4.7 | 24 | YMO-SSI |
| Schizoblastosporion starkeyi-henric | 10842 | 0.0 | 0.9 | 0.2 | 0.0 | 1.1 | 0.8 | 24 | YPDO-SSI |
| Sporopachydermia cereana | 10013 | 0.0 | 0.6 | 0.2 | 0.2 | 0.1 | 1.2 | 24 | YMO-SSI |
| Stephanoascus ciferrii | 1854 | 0.0 | 0.9 | 0.1 | 0.0 | 3.3 | 0.0 | 24 | YMO-SSI |
| Sterigmatomyces elviae | 1843 | 0.0 | 4.5 | 0.5 | 0.1 | 10.5 | 1.8 | 24 | YMO-SSI |
| Sterigmatomyces halophilus | 1488 | 0.0 | 0.0 | 0.0 | 0.8 | 0.3 | 0.0 | 24 | YMO-SSI |
| Sterigmatosporidium polymorphum | 10121 | 0.0 | 2.4 | 0.1 | 0.0 | 15.7 | 1.3 | 24 | YMO-SSI |
| Sympodiomyces parvus | 10132 | 0.0 | 3.7 | 0.1 | 0.0 | 3.0 | 0.0 | 17 | YMO-SSI |
| Sympodiomycopsis paphiopedili | 10750 | 0.0 | 1.3 | 1.0 | 0.0 | 0.8 | 1.0 | 24 | YMO-SSI |
| Trichosporon brassicae | 1584 | 0.0 | 13.0 | 0.7 | 0.0 | 13.2 | 0.0 | 24 | YMO-SSI |
| Trichosporon pullulans | 1232 | 0.2 | 10.9 | 0.2 | 0.3 | 30.5 | 1.1 | 17 | YMO-SSI |
| Trigonopsis variabilis | 0755 | 0.0 | 0.0 | 0.0 | 0.0 | 0.1 | 0.2 | 24 | YMO-SSI |
| Tsuchiyaea wingfieldii | 10204 | 0.0 | 15.3 | 0.7 | 0.0 | 17.5 | 1.4 | 24 | YMO-SSI |
| Wickerhamilla domercqiae | 1857 | 0.0 | 1.7 | 0.0 | 0.0 | 5.2 | 0.0 | 24 | YMO-SSI |

TABLE 15-continued

Production of nerolidol (NOH), farnesol (FOH) and geranylgeraniol (GGOH) (mg/L of culture solution)

| Strains | No. | | | | | | | | |
|---|---|---|---|---|---|---|---|---|---|
| *Xanthophyllomyces dendrorhous* | 10130 | 0.1 | 30.0 | 0.8 | 0.5 | 33.8 | 2.8 | 24 | YMO-SSI |
| *Zygozyma oligophaga* | 10360 | 0.1 | 6.4 | 5.3 | 0.8 | 24.3 | 5.6 | 24 | YMO-SSI |

| | | Day 3 | | | Day 9 | | | Temp. | |
|---|---|---|---|---|---|---|---|---|---|
| Strains | No. | NOH | FOH | GGOH | NOH | FOH | GGOH | (° C.) | Medium |
| *Aciculoconidium aculeatum* | IFO 10124 | 0.0 | 21.3 | 1.4 | 0.0 | 26.4 | 2.3 | 24 | YMO-SSI |
| *Bullera pseudoalba* | IFO 10179 | 0.0 | 11.0 | 2.0 | 0.0 | 40.7 | 15.0 | 24 | YMO-SSI |
| *Candida albicans* | IFO 1060 | 0.2 | 108.8 | 3.5 | 0.8 | 32.9 | 4.7 | 30 | YMO-SSI |
| *Candida glabrata* | IFO 0741 | 0.3 | 19.6 | 0.6 | 3.2 | 70.1 | 4.2 | 30 | YMO-SSI |
| *Candida guilliermondii* | IFO 0566 | 0.0 | 3.9 | 0.8 | 0.0 | 4.2 | 1.1 | 30 | YMO-SSI |
| *Candida intermedia* | IFO 0761 | 0.0 | 56.2 | 2.5 | 0.1 | 87.0 | 6.2 | 30 | YMO-SSI |
| *Candida kefyr* | IFO 0706 | 0.3 | 28.2 | 2.0 | 0.7 | 15.8 | 2.9 | 30 | YMO-SSI |
| *Candida krusei* | IFO 0941 | 0.5 | 37.9 | 4.0 | 3.7 | 7.8 | 8.0 | 30 | YMO-SSI |
| *Candida tenuis* | IFO 0716 | 0.0 | 2.2 | 0.2 | 0.0 | 31.2 | 2.2 | 30 | YMO-SSI |
| *Candida utilis* | IFO 0619 | 0.2 | 42.2 | 5.5 | 0.8 | 52.5 | 11.1 | 30 | YMO-SSI |
| *Cryptococcus humicola* | IFO 0753 | 0.2 | 6.3 | 2.0 | 0.0 | 0.3 | 3.3 | 30 | YMO-SSI |
| *Cryptococcus terreus* | IFO 0727 | 0.0 | 1.2 | 0.1 | 0.2 | 1.9 | 0.3 | 30 | YMO-SSI |
| *Debaryomyces castellii* | IFO 1359 | 0.0 | 11.4 | 1.1 | 0.0 | 26.8 | 4.6 | 30 | YMO-SSI |
| *Fellomyces penicillatus* | IFO 10119 | 0.0 | 2.9 | 0.3 | 0.1 | 45.7 | 4.4 | 24 | YMO-SSI |
| *Filobasidium capsuligenum* | IFO 1185 | 0.0 | 51.0 | 1.1 | 0.2 | 106.6 | 3.6 | 24 | YMO-SSI |
| *Filobasidium uniguttulatum* | IFO 0699 | 0.0 | 28.7 | 1.3 | 0.4 | 85.4 | 8.9 | 24 | YMO-SSI |
| *Kloeckera corticis* | IFO 0633 | 0.4 | 42.8 | 2.3 | 1.2 | 62.1 | 8.2 | 30 | YMO-SSI |
| *Holtermannia corniformis* | IFO 10742 | 0.0 | 25.4 | 2.8 | 1.1 | 50.7 | 8.4 | 24 | YMO-SSI |
| *Kluyveromyces marxianus* | IFO 0617 | 0.0 | 16.6 | 0.8 | 0.4 | 35.1 | 5.0 | 30 | YMO-SSI |
| *Phaffia rhodozyma* | ATCC 66270 | 0.0 | 2.2 | 0.1 | 0.5 | 108.7 | 5.8 | 24 | YMO-SSI |
| *Pichia anomala* | IFO 0146 | 0.2 | 34.8 | 2.6 | 0.2 | 7.4 | 4.3 | 30 | YMO-SSI |
| *Pichia fabianii* | IFO 1254 | 0.0 | 14.3 | 1.5 | 0.2 | 0.1 | 4.2 | 30 | YMO-SSI |
| *Pichia farinosa* | IFO 1003 | 0.0 | 3.2 | 0.6 | 0.0 | 11.1 | 1.8 | 30 | YMO-SSI |
| *Pichia jadinii* | IFO 0987 | 0.0 | 23.1 | 2.0 | 0.1 | 24.6 | 8.3 | 30 | YMO-SSI |
| *Pichia polymorpha* | IFO 0195 | 0.3 | 21.8 | 3.2 | 0.4 | 0.6 | 5.2 | 30 | YMO-SSI |
| *Pichia silvicola* | IFO 0807 | 0.2 | 10.6 | 1.6 | 0.8 | 29.0 | 4.2 | 30 | YMO-SSI |
| *Rhodotorula glutinis* | IFO 0695 | 0.0 | 3.8 | 0.2 | 0.0 | 3.4 | 0.3 | 30 | YMO-SSI |
| *Rhodotorula minuta* | IFO 0715 | 0.3 | 6.6 | 12.0 | 3.4 | 5.0 | 0.7 | 30 | YMO-SSI |
| *Rhodotorula rubra* | IFO 0870 | 0.3 | 5.5 | 10.8 | 3.5 | 4.4 | 26.4 | 30 | YMO-SSI |
| *Saccharomyces cerevisiae* | IFO 0258 | 0.0 | 22.3 | 0.6 | 0.4 | 77.5 | 1.9 | 30 | YMO-SSI |
| *Saccharomyces cerevisiae* | IFO 2347 | 0.0 | 18.8 | 0.7 | 0.1 | 36.5 | 1.4 | 30 | YMO-SSI |
| *Saccharomycodes ludwigii* | IFO 10036 | 0.0 | 3.3 | 0.2 | 0.1 | 15.5 | 0.4 | 24 | YMO-SSI |
| *Saccharomycopsis fermentans* | IFO 10772 | 0.1 | 41.4 | 1.9 | 0.3 | 37.9 | 3.1 | 24 | YMO-SSI |
| *Sporidiobolus samonicolor* | IFO 1035 | 0.1 | 7.9 | 1.1 | 0.1 | 42.3 | 6.4 | 30 | YMO-SSI |
| *Sporobolomyces salmonicolor* | IFO 0374 | 0.1 | 28.8 | 3.4 | 0.5 | 35.7 | 14.4 | 30 | YMO-SSI |
| *Trichosporiella flavificans* | IFO 1573 | 0.0 | 0.0 | 0.0 | 0.2 | 31.5 | 3.0 | 24 | YMO-SSI |
| *Trichosporon penicillatum* | JCM 2171 | 0.0 | 1.7 | 0.6 | 0.1 | 1.7 | 0.0 | 30 | YMO-SSI |
| *Williopsis californica* | IFO 0800 | 10.1 | 95.7 | 4.7 | 10.5 | 90.1 | 5.2 | 24 | YMO-SSI |
| *Willopsis saturnus* | IFO 0895 | 0.5 | 59.1 | 9.0 | 1.6 | 69.2 | 13.1 | 30 | YMO-SSI |
| *Yamadazyma farinosa* | IFO 0459 | 0.0 | 6.2 | 0.8 | 0.0 | 20.8 | 2.2 | 30 | YMO-SSI |
| *Zygoascus hellenicus* | IFO 10184 | 0.0 | 3.9 | 0.1 | 0.0 | 32.4 | 2.7 | 24 | YMO-SSI |

The present invention enables prenyl alcohol to be highly produced in and effectively secreted from prenyl alcohol-producing cells by culturing the cells in a medium with an increased sugar content in the presence of at least one member selected from the group consisting of a surfactant, a fat or oil, and a terpene.

All publications, patents and patent applications cited herein are incorporated herein by reference in their entirety.

What is claimed is:

1. A method for producing a prenyl alcohol, which comprises
    culturing cells of a strain of *Saccharomyces* that secretes prenyl alcohol in a nutrient medium having a sugar content of 2% to 7% and containing at least one oil selected from the group consisting of soybean oil, fish oil, almond oil and olive oil in a concentration of about 0.01% or more, to produce, accumulate, and secrete prenyl alcohol from the cells; and
    collecting the prenyl alcohol.

2. The method according to claim 1, wherein prenyl alcohol is at least one of geranylgeraniol, farnesol and nerolidol.

3. The method of claim 1, wherein the medium further comprises a terpene.

4. The method of claim 1, wherein the medium further comprises a surfactant.

* * * * *